(12) United States Patent
Marco et al.

(10) Patent No.: US 8,845,673 B2
(45) Date of Patent: Sep. 30, 2014

(54) BIOERODIBLE SELF-DEPLOYABLE INTRAGASTRIC IMPLANTS AND METHODS FOR USE THEREOF

(75) Inventors: Doron Marco, Tel-Aviv (IL); Shimon Eckhouse, Haifa (IL)

(73) Assignee: Tulip Medical Ltd., Herzliya (IL)

( * ) Notice: Subject to any disclaimer, the term of this patent is extended or adjusted under 35 U.S.C. 154(b) by 532 days.

(21) Appl. No.: 12/841,314

(22) Filed: Jul. 22, 2010

(65) Prior Publication Data

US 2011/0015666 A1 Jan. 20, 2011

Related U.S. Application Data

(63) Continuation of application No. 11/788,574, filed on Apr. 19, 2007, now Pat. No. 7,785,291, which is a continuation-in-part of application No. 11/519,508, filed on Sep. 11, 2006, now Pat. No. 7,699,863, which is a continuation-in-part of application No. PCT/IL2006/000276, filed on Mar. 1, 2006.

(30) Foreign Application Priority Data

Mar. 1, 2005 (IL) .......................................... 167194
Jul. 13, 2006 (IL) .......................................... 176856

(51) Int. Cl.
- *A61M 29/00* (2006.01)
- *A61F 5/00* (2006.01)
- *A61F 2/02* (2006.01)
- *A61F 2/04* (2013.01)

(52) U.S. Cl.
CPC ................. *A61F 2/02* (2013.01); *A61F 5/0036* (2013.01); *A61F 5/003* (2013.01); *A61F 2210/0004* (2013.01); *A61F 2002/044* (2013.01)

USPC ........................................................ 606/192

(58) Field of Classification Search
USPC ........ 604/890.1, 891.1, 892.1, 65–67, 23–26, 604/45, 143, 145, 146, 147, 197.01; 606/192

See application file for complete search history.

(56) References Cited

U.S. PATENT DOCUMENTS

| 2,470,665 A | 5/1949 | Stiehl |
| 3,674,014 A | 7/1972 | Tillander |

(Continued)

FOREIGN PATENT DOCUMENTS

| DE | 10304614 A1 | 8/2004 |
| EP | 0103481 | 3/1984 |

(Continued)

OTHER PUBLICATIONS

Japanese Office Action Translation dated May 23, 2012 for Japanese Patent No. 2009-511077.

(Continued)

*Primary Examiner* — Manuel Mendez
(74) *Attorney, Agent, or Firm* — Fleit Gibbons Gutman Bongini & Bianco PL; Martin Fleit; Paul D. Bianco

(57) ABSTRACT

Described herein are bioerodible, biodegradable, or digestible self-deploying intragastric implants that may be swallowed. Once swallowed, the implants undergo self-expansion in the stomach and apply a suitable pressure against the stomach wall to provide a feeling of satiety to the individual. The implants then dissolve or are disassembled perhaps using gastric liquids and pass out of the stomach. Methods of using the devices, perhaps for an individual participating in a dietary control regimen, are described.

47 Claims, 20 Drawing Sheets

(56) References Cited

U.S. PATENT DOCUMENTS

| | | | |
|---|---|---|---|
| 3,774,596 A | | 11/1973 | Cook |
| 3,786,813 A | * | 1/1974 | Michaels .................. 604/892.1 |
| 3,840,009 A | * | 10/1974 | Michaels et al. .......... 604/892.1 |
| 3,911,098 A | | 10/1975 | Capozza |
| 4,133,315 A | | 1/1979 | Berman et al. |
| 4,140,755 A | | 2/1979 | Sheth et al. |
| 4,142,526 A | | 3/1979 | Zaffaroni et al. |
| 4,167,558 A | | 9/1979 | Sheth et al. |
| 4,203,439 A | * | 5/1980 | Theeuwes .................. 604/892.1 |
| 4,207,890 A | | 6/1980 | Mamajek et al. |
| 4,236,521 A | | 12/1980 | Lauterjung |
| 4,246,893 A | | 1/1981 | Berson |
| 4,308,250 A | | 12/1981 | Griffin et al. |
| 4,311,146 A | | 1/1982 | Wonder |
| 4,416,267 A | | 11/1983 | Garren et al. |
| 4,447,227 A | | 5/1984 | Kotsanis |
| 4,485,805 A | | 12/1984 | Foster, Jr. |
| 4,501,264 A | | 2/1985 | Rockey |
| 4,546,143 A | | 10/1985 | Weil et al. |
| 4,607,618 A | | 8/1986 | Angelchik |
| 4,692,152 A | * | 9/1987 | Emde ...................... 604/164.01 |
| 4,694,827 A | * | 9/1987 | Weiner et al. .................. 606/192 |
| 4,723,547 A | * | 2/1988 | Kullas et al. .................. 606/185 |
| 4,739,758 A | | 4/1988 | Lai et al. |
| 4,753,976 A | | 6/1988 | Yoshioka et al. |
| 4,767,627 A | | 8/1988 | Caldwell et al. |
| 4,790,429 A | | 12/1988 | Fukushima |
| 4,812,315 A | | 3/1989 | Tarabishi |
| 4,878,905 A | | 11/1989 | Blass |
| 4,899,747 A | | 2/1990 | Garren et al. |
| 4,925,446 A | * | 5/1990 | Garay et al. ............. 604/103.02 |
| 4,968,294 A | | 11/1990 | Salama |
| 4,984,564 A | | 1/1991 | Yuen |
| 5,084,061 A | | 1/1992 | Gau et al. |
| 5,129,915 A | * | 7/1992 | Cantenys ...................... 606/192 |
| 5,167,626 A | | 12/1992 | Casper |
| 5,206,030 A | | 4/1993 | Wheatley et al. |
| 5,234,454 A | | 8/1993 | Bangs |
| 5,259,399 A | | 11/1993 | Brown |
| 5,443,505 A | | 8/1995 | Wong et al. |
| 5,520,609 A | | 5/1996 | Moll et al. |
| 5,558,642 A | | 9/1996 | Schweich, Jr. et al. |
| 5,649,978 A | | 7/1997 | Samson |
| 5,738,629 A | | 4/1998 | Moll et al. |
| 5,750,585 A | | 5/1998 | Park et al. |
| 5,770,181 A | | 6/1998 | Kirkland |
| 5,783,212 A | | 7/1998 | Fassihi et al. |
| 5,836,871 A | | 11/1998 | Wallace et al. |
| 5,893,826 A | | 4/1999 | Salama |
| 5,972,369 A | | 10/1999 | Roorda et al. |
| 5,989,590 A | * | 11/1999 | Wong et al. .................... 424/473 |
| 5,993,473 A | | 11/1999 | Chan et al. |
| 6,079,871 A | | 6/2000 | Jonas et al. |
| 6,271,278 B1 | | 8/2001 | Park et al. |
| 6,287,332 B1 | | 9/2001 | Bolz et al. |
| 6,454,785 B2 | | 9/2002 | De Hoyos Garza |
| 6,503,264 B1 | | 1/2003 | Birk |
| 6,517,559 B1 | | 2/2003 | O'Connell |
| 6,579,301 B1 | * | 6/2003 | Bales et al. .................... 606/191 |
| 6,579,310 B1 | | 6/2003 | Cox et al. |
| 6,605,037 B1 | | 8/2003 | Moll et al. |
| 6,675,809 B2 | | 1/2004 | Stack et al. |
| 6,726,920 B1 | * | 4/2004 | Theeuwes et al. ............. 424/423 |
| 6,733,512 B2 | | 5/2004 | McGhan |
| 6,755,869 B2 | | 6/2004 | Geitz |
| 6,833,488 B2 | | 12/2004 | Bucevschi et al. |
| 6,845,776 B2 | | 1/2005 | Stack et al. |
| 6,981,980 B2 | * | 1/2006 | Sampson et al. .............. 606/192 |
| 7,009,634 B2 | | 3/2006 | Iddan et al. |
| 7,033,373 B2 | | 4/2006 | de la Torre et al. |
| 7,052,488 B2 | | 5/2006 | Uhland |
| 7,056,305 B2 | | 6/2006 | Garza Alvarez |
| 7,066,945 B2 | | 6/2006 | Hashiba et al. |
| 7,111,627 B2 | | 9/2006 | Stack et al. |
| 7,112,186 B2 | | 9/2006 | Shah |
| 7,335,210 B2 | | 2/2008 | Smit |
| 7,632,291 B2 | | 12/2009 | Stephens et al. |
| 7,699,863 B2 | | 4/2010 | Marco |
| 7,699,883 B2 | | 4/2010 | Douglas |
| 7,785,291 B2 | | 8/2010 | Marco et al. |
| 7,931,693 B2 | | 4/2011 | Biomoeller |
| 8,267,888 B2 | | 9/2012 | Marco et al. |
| 2003/0040804 A1 | | 2/2003 | Stack et al. |
| 2003/0040808 A1 | | 2/2003 | Stack et al. |
| 2003/0109935 A1 | | 6/2003 | Geitz |
| 2003/0199989 A1 | | 10/2003 | Stack et al. |
| 2003/0199990 A1 | | 10/2003 | Stack et al. |
| 2003/0199991 A1 | | 10/2003 | Stack et al. |
| 2003/0212452 A1 | | 11/2003 | Zadno-Azizi et al. |
| 2004/0129186 A1 | | 7/2004 | Curiger |
| 2004/0143342 A1 | | 7/2004 | Stack et al. |
| 2004/0186502 A1 | * | 9/2004 | Sampson et al. .............. 606/191 |
| 2004/0192582 A1 | | 9/2004 | Burnett et al. |
| 2005/0216074 A1 | | 9/2005 | Sahatjian et al. |
| 2006/0018948 A1 | | 1/2006 | Guire et al. |
| 2006/0025799 A1 | | 2/2006 | Basu |
| 2006/0058829 A1 | | 3/2006 | Sampson et al. |
| 2006/0111632 A1 | | 5/2006 | Chen |
| 2006/0111777 A1 | | 5/2006 | Chen |
| 2006/0155259 A1 | | 7/2006 | MacLay |
| 2006/0178726 A1 | | 8/2006 | Douglas |
| 2006/0222681 A1 | | 10/2006 | Richard |
| 2006/0282107 A1 | | 12/2006 | Hashiba et al. |
| 2007/0078476 A1 | | 4/2007 | Hull et al. |
| 2007/0100367 A1 | | 5/2007 | Quijano et al. |
| 2007/0100368 A1 | | 5/2007 | Quijano et al. |
| 2007/0100369 A1 | | 5/2007 | Cragg et al. |
| 2007/0104754 A1 | | 5/2007 | Sterling et al. |
| 2007/0104755 A1 | | 5/2007 | Sterling et al. |
| 2007/0106372 A1 | | 5/2007 | Osborne et al. |
| 2007/0118168 A1 | | 5/2007 | Lointier et al. |
| 2007/0135829 A1 | | 6/2007 | Paganon |
| 2007/0224234 A1 | | 9/2007 | Steckel et al. |
| 2007/0249900 A1 | | 10/2007 | Wilson et al. |
| 2007/0250102 A1 | | 10/2007 | Makower et al. |
| 2007/0250103 A1 | | 10/2007 | Makower et al. |
| 2007/0265709 A1 | | 11/2007 | Rajan et al. |
| 2007/0293716 A1 | | 12/2007 | Baker et al. |
| 2008/0107732 A1 | | 5/2008 | Dharmadhikari et al. |
| 2008/0206145 A1 | | 8/2008 | Afargan et al. |
| 2008/0208356 A1 | | 8/2008 | Stack |
| 2008/0269797 A1 | | 10/2008 | Stack et al. |
| 2009/0035367 A1 | | 2/2009 | Mintchev et al. |
| 2009/0098198 A1 | | 4/2009 | Rousso et al. |
| 2009/0177215 A1 | | 7/2009 | Stack et al. |
| 2009/0182424 A1 | | 7/2009 | Marco |
| 2009/0299487 A1 | | 12/2009 | Stack et al. |
| 2009/0304773 A1 | | 12/2009 | Tsabari et al. |
| 2009/0304768 A1 | | 12/2009 | Lapidot et al. |
| 2009/0318649 A1 | | 12/2009 | Bucevschi |
| 2011/0015665 A1 | | 1/2011 | Marco |
| 2011/0015666 A1 | | 1/2011 | Marco et al. |
| 2011/0022072 A1 | | 1/2011 | Marco |
| 2011/0040318 A1 | | 2/2011 | Marco |
| 2011/0045665 A1 | | 2/2011 | Trentzsch |

FOREIGN PATENT DOCUMENTS

| | | |
|---|---|---|
| JP | H03500258 A | 1/1991 |
| JP | 2006522643 A | 10/2006 |
| WO | 9925418 | 5/1999 |
| WO | 0240081 | 5/2002 |
| WO | 02091961 | 11/2002 |
| WO | 03015745 | 2/2003 |
| WO | 03017882 | 3/2003 |
| WO | 03028477 | 4/2003 |
| WO | 2004064680 | 8/2004 |
| WO | 2004084763 | 10/2004 |
| WO | 2005018417 | 3/2005 |
| WO | 2005039458 | 5/2005 |
| WO | 2005082296 | 9/2005 |
| WO | 2005097012 | 10/2005 |
| WO | 2005101983 | 11/2005 |
| WO | 2005120363 | 12/2005 |

(56) References Cited

FOREIGN PATENT DOCUMENTS

| WO | 2006020929 | 2/2006 |
|---|---|---|
| WO | 2006044640 | 4/2006 |
| WO | 2006047882 | 5/2006 |
| WO | 2006055839 | 5/2006 |
| WO | 2006063593 | 6/2006 |
| WO | 2006072948 | 7/2006 |
| WO | 2007017842 | 2/2007 |
| WO | 2007083309 | 7/2007 |
| WO | 2007084724 | 7/2007 |
| WO | 2007093999 | 8/2007 |
| WO | 2007115169 | 10/2007 |
| WO | 2007136735 | 11/2007 |

OTHER PUBLICATIONS

Office Action dated Nov. 10, 2011, response filed May 10, 2012, Notice of Allowance dated May 23, 2012 for U.S. Appl. No. 12/841,267.
International Search Report published Apr. 30, 2009 for PCT/IL06/0276 filed Mar. 1, 2006.
Written Opinion published Mar. 20, 2009 for PCT/IL06/0276 filed Mar. 1, 2006.
International Preliminary Report on Patentability published Mar. 24, 2009 for PCT/IL06/0276 filed Mar. 1, 2006.
International Search Report published Feb. 28, 2008 for PCT/US07/11882 filed May 18, 2007 (claiming priority to U.S. Appl. No. 11/788,574).
Written Opinion published Nov. 18, 2008 for PCT/US07/11882 filed May 18, 2007 (claiming priority to U.S. Appl. No. 11/788,574).
International Preliminary Report on Patentability published Nov. 18, 2008 for PCT/US07/11882 filed May 18, 2007 (claiming priority to U.S. Appl. No. 11/788,574).
Office action dated Feb. 7, 201 3 for U.S. Appl. No. 12/841,283.
Response dated Jul. 8, 2013 for U.S. Appl. No. 12/841,283.
For U.S. Appl. No. 12/841,298: office actions dated Aug. 4, 2012; response dated Nov. 14, 2012; notice of allowance dated Dec. 18, 2012; RCE dated Feb. 19, 2013.
Response to office action, filed Apr. 30, 2014 for U.S. Appl. No. 12/841,283.
Response to office action, filed Apr. 21, 2014 for U.S. Appl. No. 12/841,298.
Response to office action, filed Jan. 21, 2014 for U.S. Appl. No. 12/841,314.
Ratner, Introduction to materials science, Biomaterials Science, Second Edition, 2004.
Office Action dated Oct. 31, 2013 for U.S. Appl. No. 12/841,283, filed Jul. 22, 2010.
Office Action dated Oct. 21, 2013 for U.S. Appl. No. 12/841,298, filed Jul. 22, 2010.

* cited by examiner

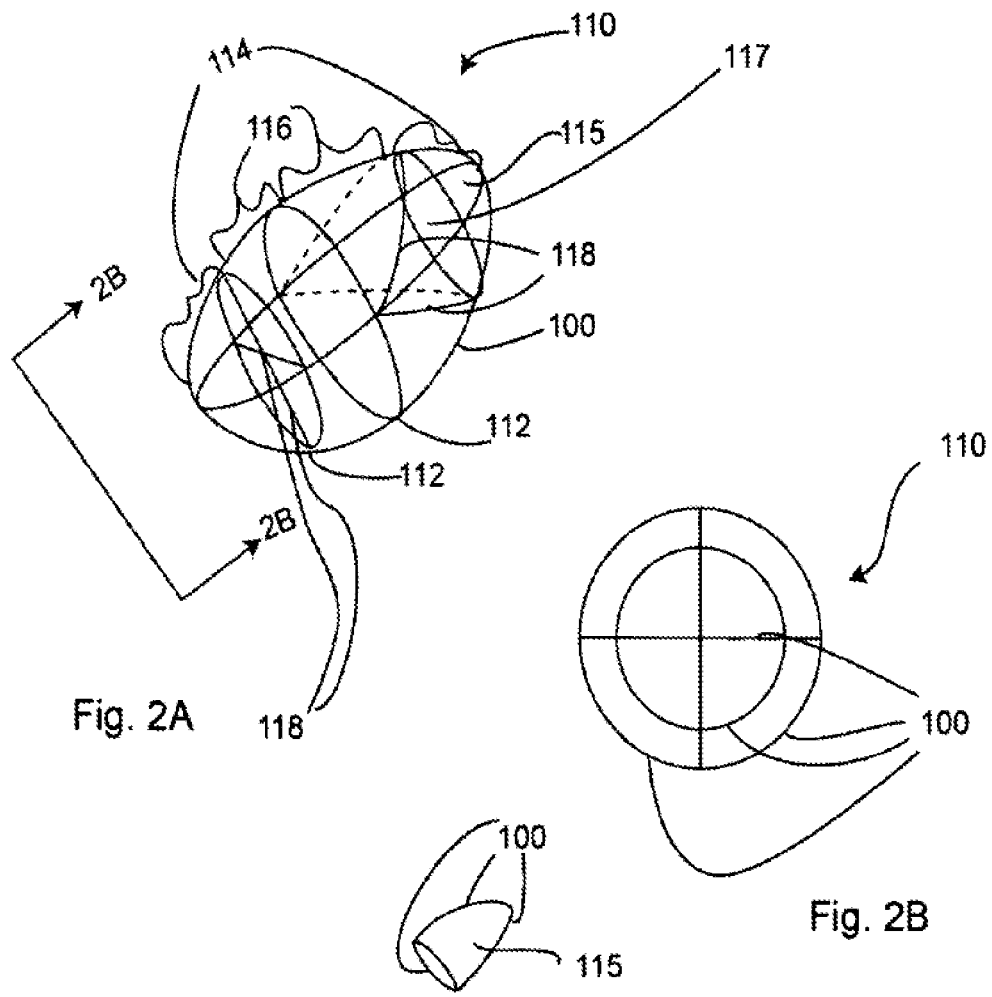
Fig. 2A
Fig. 2B
Fig. 2C
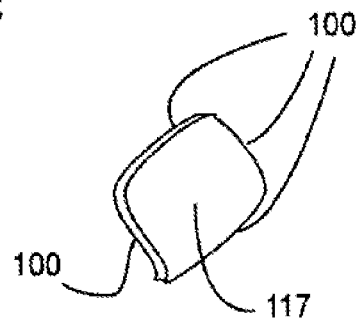
Fig. 2D

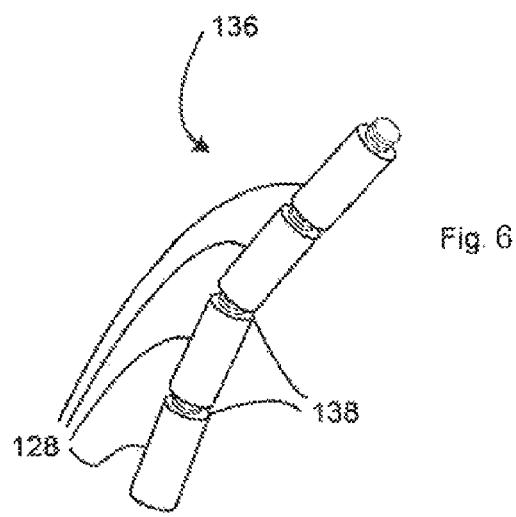
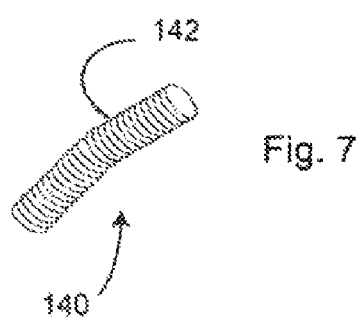
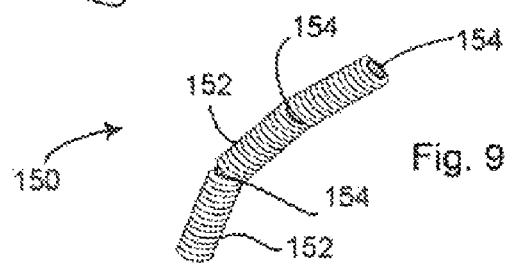
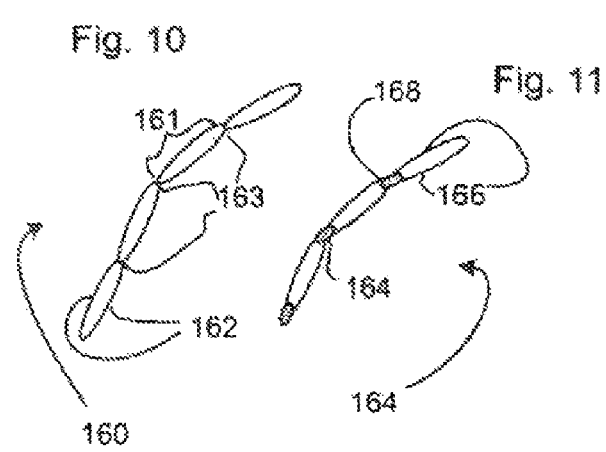
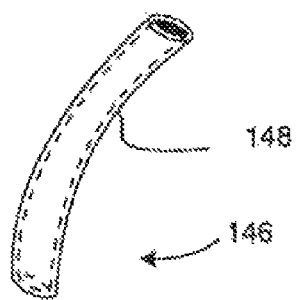

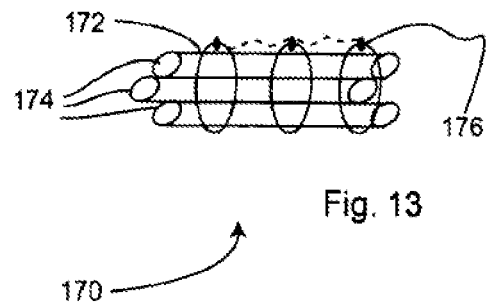
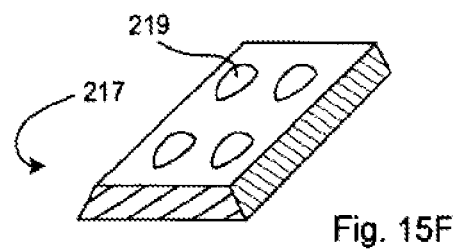
Fig. 13
Fig. 15F
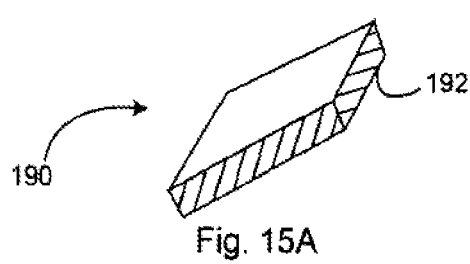
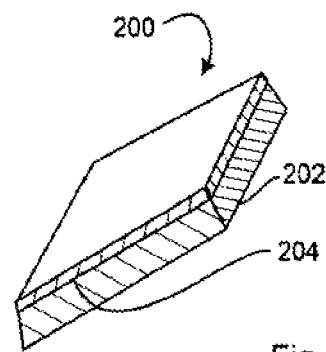
Fig. 15A
Fig. 15C
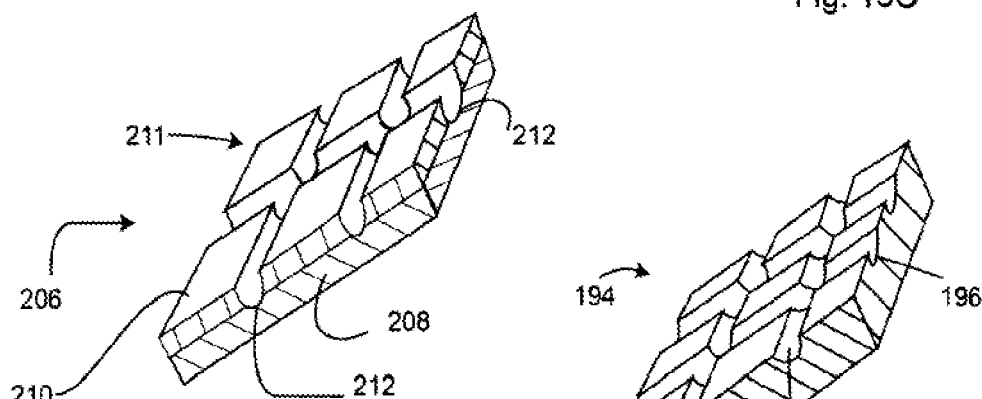
Fig. 15D
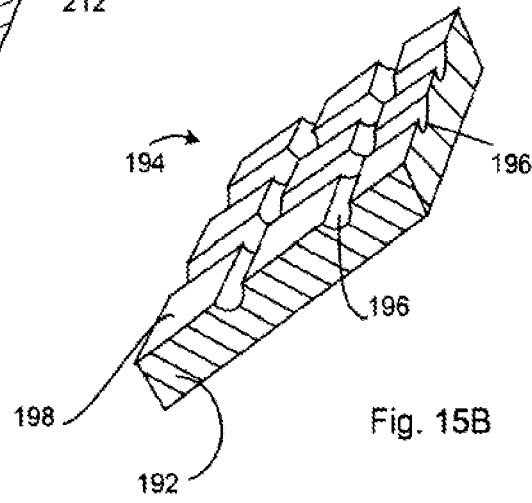
Fig. 15B
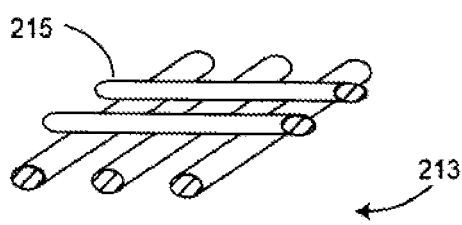
Fig. 15E

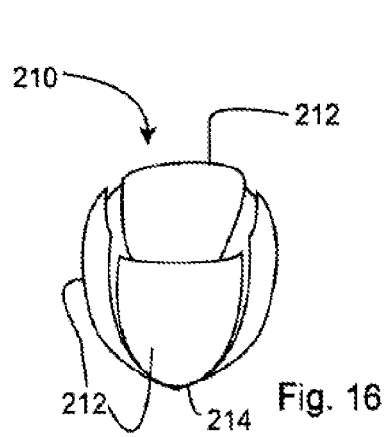
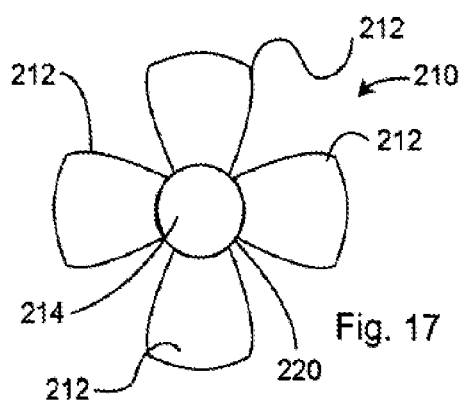
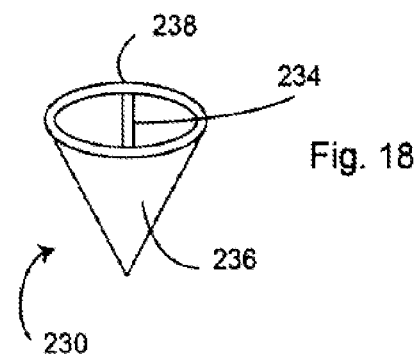
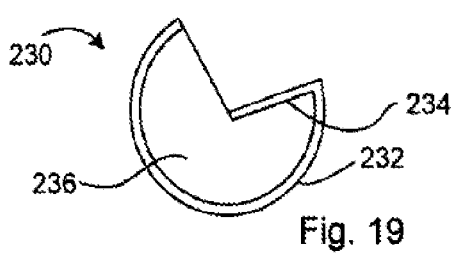
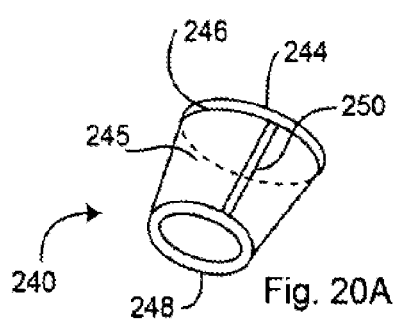
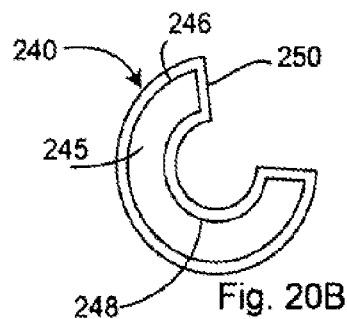
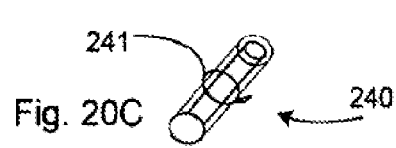
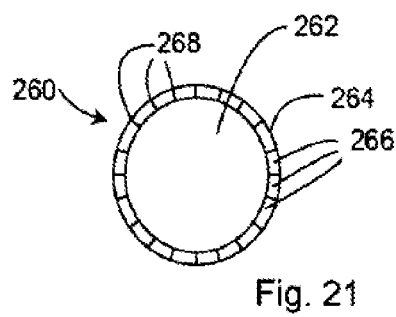

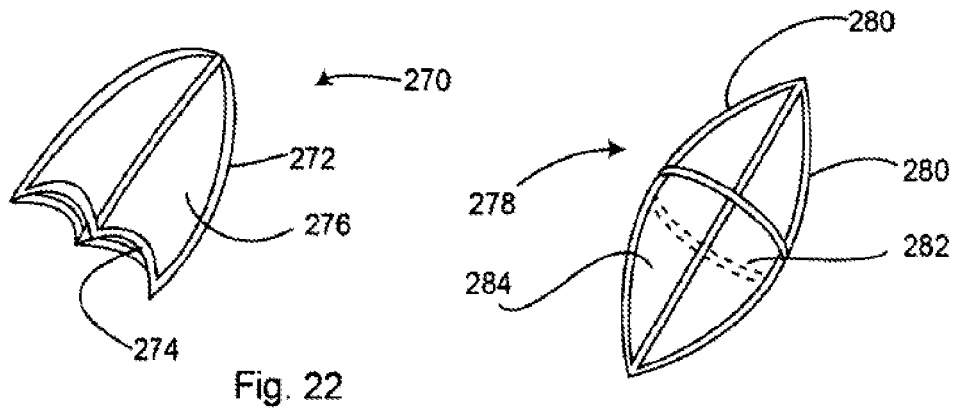
Fig. 22
Fig. 23
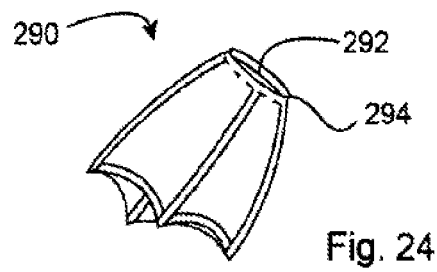
Fig. 24
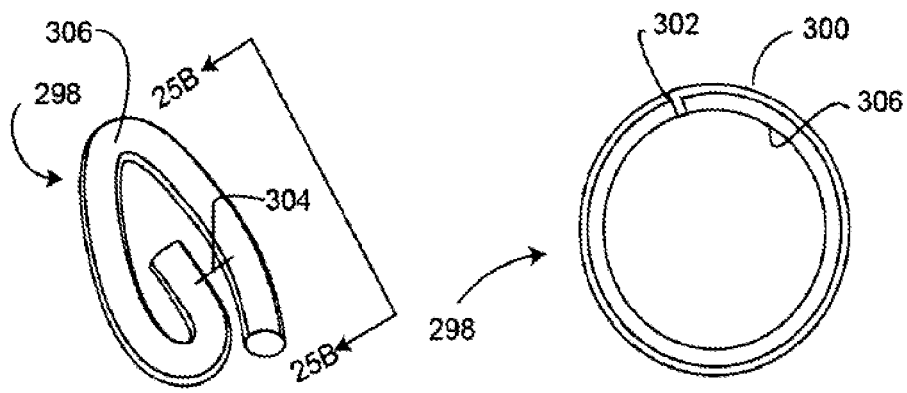
Fig. 25A
Fig. 25B

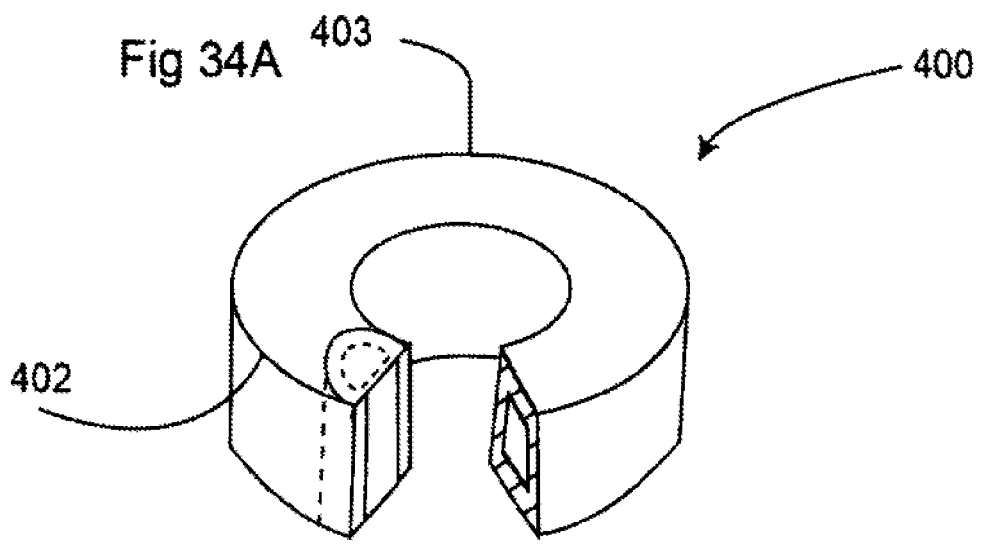
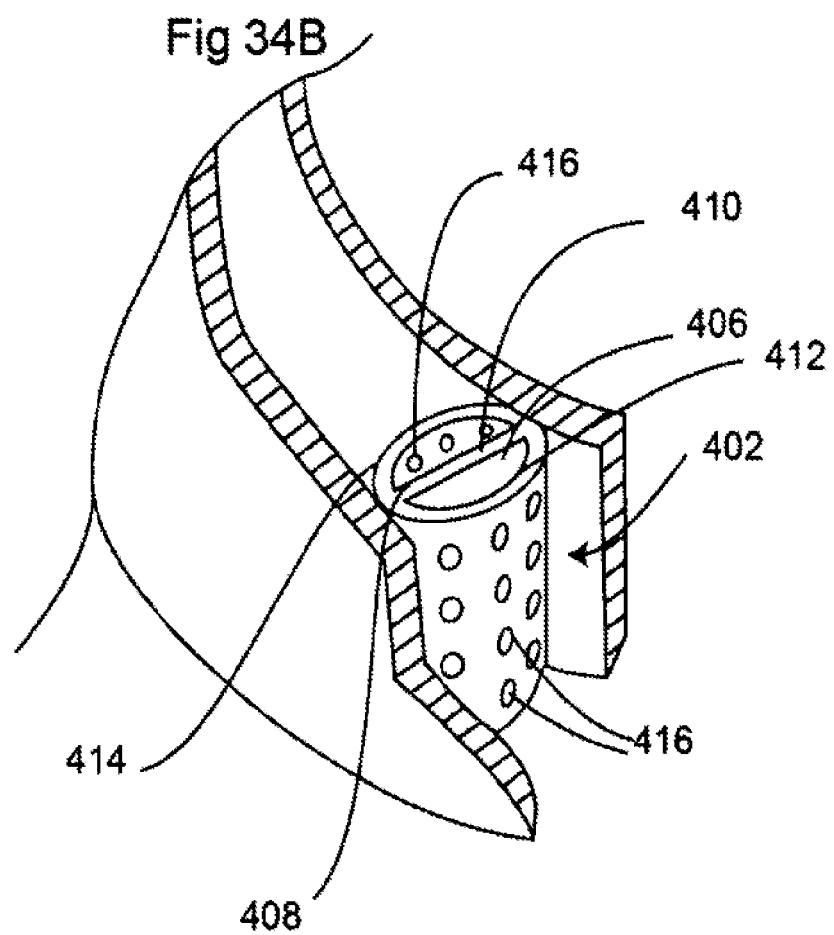

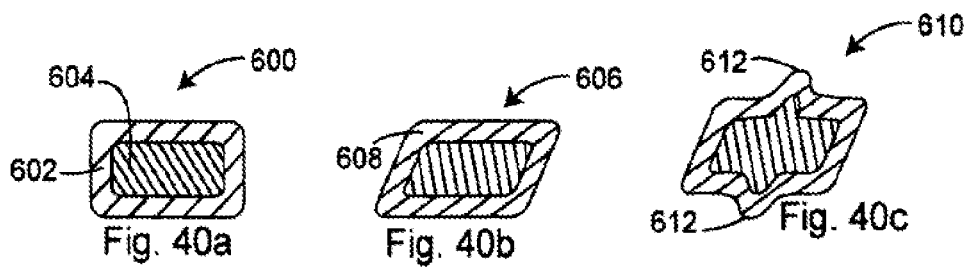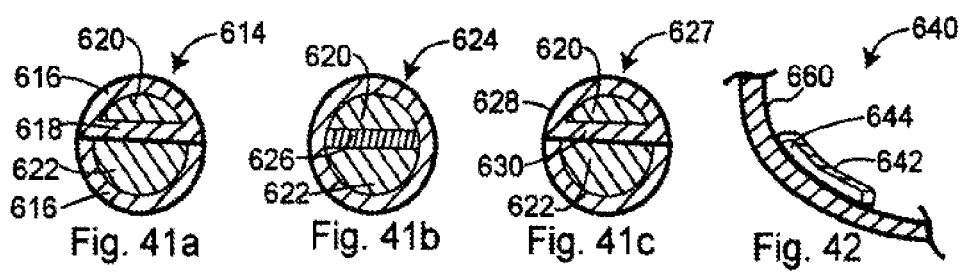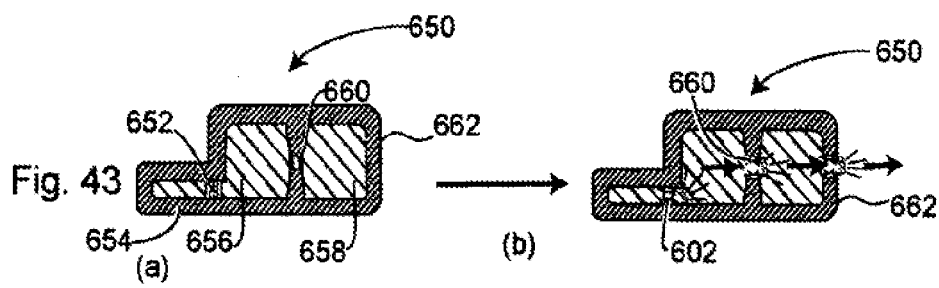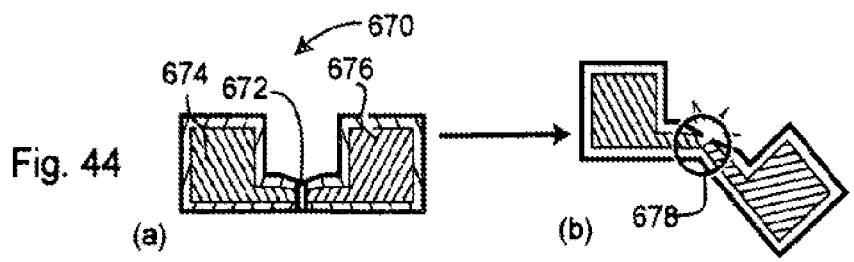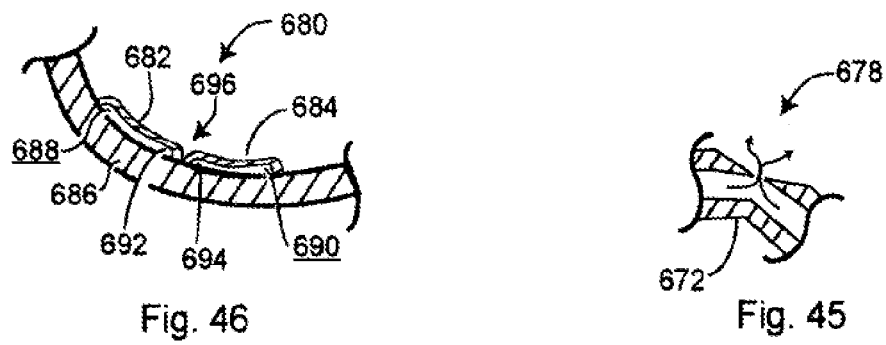

US 8,845,673 B2

BIOERODIBLE SELF-DEPLOYABLE INTRAGASTRIC IMPLANTS AND METHODS FOR USE THEREOF

RELATED APPLICATIONS

This application is a continuation of U.S. Ser. No. 11/788,574, now U.S. Pat. No. 7,785,291, which is a continuation-in-part of U.S. Ser. No. 11/519,508, filed Sep. 11, 2006 (now U.S. Pat. No. 7,699,863), which is a continuation-in-part of International Application No. PCT/IL2006/000276, filed Mar. 1, 2006, claiming priority from Israeli Application No. 167,194, filed Mar. 1, 2005, and which U.S. application further claims priority under 35 USC 119(a) from Israeli Application No. 176,856, filed Jul. 13, 2006. The entirety of each of these documents is incorporated by reference for all reasons.

FIELD

Described herein are bioerodible, biodegradable, or digestible self-deploying intragastric implants that may be swallowed. Once swallowed, the implants undergo self-expansion in the stomach and apply a suitable pressure against the stomach wall to provide a feeling of satiety to the individual. The internal components that provide gas for expansion of the implant may be deployed by mechanical mixing, fracture of an frangible component, manual manipulation, or the like. The implants then dissolve or are disassembled perhaps using gastric liquids and pass out of the stomach. Methods of using the devices, perhaps for an individual participating in a dietary control regimen, are described.

BACKGROUND

Obesity is a major health problem in developed countries. In the United States, the complications of obesity affect nearly one in five individuals at an annual cost of approximately $40 billion. Except for rare pathological conditions, weight gain is often directly correlated to overeating.

One strategy for controlling the individual's food intake is via the use of intragastric volume-occupying devices. Such devices are placed in the stomach and occupy a portion of its interior. Properly placed and sized, the intragastric volumes provide the patient with a feeling of satiety after having eaten only a smaller amount of food. Typically, the individual's caloric intake is thus diminished due to the subjective feeling of fullness. There are a number of available volume-occupying devices. Many must be introduced using surgical or other complex gastric procedures.

Intragastric balloons have been in clinical use for several years. Their success in the treatment of certain individuals with morbid obesity is well accepted.

Published U.S. Patent Application No. 2004/0186502, U.S. Pat. No. 6,981,980, and published PCT application WO/2006/020929, to Sampson et al, each disclose inflatable, intragastric volume-occupying balloons including a valve that provides fluid communication into the balloon from outside the body. The '502 application further discloses a method for occupying some amount of stomach volume comprising the step of inserting the deflated balloon into the stomach through the esophagus, inflating the balloon by introducing an activating liquid through the self-sealing valve. Each document describes selection of polymers allowing gastric erosion of the balloon and causing its subsequent deflation.

Published PCT Application WO/2006/044640, to Baker et al, shows an implant used as a bariatric device situated along certain walls of the stomach to induce a feeling of satiation.

Published U.S. Patent Application 2004/0192582, to Burnett et al, shows a composition and a device that expands in the stomach after swallowing and provide a temporary, erodible volume and consequent diminution of gastric volume in the stomach.

U.S. Pat. Nos. 6,271,278 and 5,750,585, each to Park et al, show compositions of swellable, superabsorbant-hydrogel composites that may be used in gastric retention treatments for obesity.

U.S. Pat. No. 4,607,618, to Angelchik, discloses an intragastric device made up of semi-rigid skeleton members, collapsible to a shape, and having dimensions suitable for endoscopic insertion into the stomach through the esophagus.

U.S. Pat. No. 5,129,915, to Cantenys, relates to an intragastric balloon that is intended to be swallowed and that inflates automatically under the effect of temperature. The Cantenys patent lists three ways that an intragastric balloon might be inflated by a change in temperature. First, a composition of a solid acid and of a non-toxic carbonate or bicarbonate is temporarily kept from the fluid in the stomach by a coating of chocolate, cocoa paste, or cocoa butter. The chocolate coating is selected to melt at body temperature. Secondly, a citric acid and alkaline bicarbonate composition coated a coating of non-toxic vegetable or animal fat melting at body temperature may be used. When in the presence of water, the composition is said to produce the same result as does the earlier-discussed composition. Third, the solid acid and non-toxic carbonate or bicarbonate composition may be temporarily isolated from water by an isolation pouch of a low-strength synthetic material which is to break immediately upon swallowing. Breaking the isolation pouches causes the acid, carbonate or bicarbonate, and water to mix and to react, thereby inflating the balloon. The balloon itself is said to be made up of a modestly porous, but non-digestible material that allows slow deflation.

WO/2005/039458 shows a gastric constriction device that is to be mounted exterior to the stomach and cause feelings of satiation due to pressure on the vigil nerves of the stomach.

WO/2005/101983, to Dharmadhikari, shows an expandable composition that may be used as a gastric retention system, with or without the presence of ancillary drugs.

U.S. Pat. No. 5,783,212, to Fasihi et al, shows an expandable, erodible polymeric composition that may be used in drug delivery systems.

U.S. Pat. No. 6,733,512, to McGhan, describes an intragastric balloon having erodible patches that allow self-deflation of the balloon after a chosen period of residence in the stomach.

None of the cited documents discloses the bioerodible intragastric implant deliverable to the stomach by conventional oral administration that is described below.

SUMMARY

Described herein are devices for and related methods for curbing appetite and for treating obesity. These treatments may be used in providing selective medical care and obesity therapy and are specifically suited to treatment of an individual patient while taking into account an individual's eating habits; differences in the individual's daytime and nighttime behavior; physiological and mental characteristics, body size, and age.

The devices include cost effective, biodegradable, self-inflating intragastric implants for curbing appetite and treating obesity, constructed from one or more discrete expandable members that are erodible in the stomach.

BRIEF DESCRIPTION OF THE DRAWINGS

FIGS. 2A and 2B show, respectively, a perspective view and an end view of one variation of an implant comprising a structural frame member. FIGS. 2C and 2D show isolated sections of the FIGS. 2A and 2B implant.

FIGS. 3-11 show perspective views of several variations of structural frame members suitable for use in this implant.

FIG. 13 shows a side view of one variation of a folded implant comprising a structural frame member, panels, and stabilizer members.

FIGS. 15A-15F show various panel structures.

FIG. 16 shows a perspective view of a variation of an implant comprising a structural frame member and panels.

FIG. 17 shows a top view of an unfolded implant comprising a structural frame member and panels.

FIG. 18 shows a perspective view of an expanded implant comprising a structural frame member and panels.

FIG. 19 shows a top view of an unfolded implant comprising a structural frame member and panels.

FIGS. 20A, 20B, and 20C show, respectively, a perspective view of a deployed implant, a top view, and a perspective view of a folded implant comprising a structural frame member and panels.

FIG. 21 shows a top view of an unfolded circular implant comprising a structural frame member and a panel.

FIGS. 22-24 show perspective views of several versions of unfolded implants each comprising a structural frame member and panels.

FIGS. 25A and 25B show, respectively, a top view and a perspective view of an unfolded coil-like implant comprising a structural frame member and panels.

FIGS. 33A to 33C-1 provides perspective views of a several inflated variations of our implant.

FIG. 33C-2 is a cross-section of the implant shown in FIG. 33C-1.

FIG. 34A is a partial cross section of an expanded implant showing an expanded hoop portion and a container, at least partially contained in the hoop, containing a composition that produced an expanding gas.

FIG. 34B is a perspective view of the container containing the expanding gas composition.

FIGS. 40A-40C show side cross-section views of frangible gas-producing components with fracturable outer shells, enclosing a single gas-producing chemical.

FIGS. 41A-41C show side cross-section views of frangible gas-producing components with various walls that are fracturable, enclosing two gas-producing chemicals.

FIG. 42 shows a side cross-section view of a frangible gas-producing component with a single fracturable outer shell, enclosing a single gas-producing chemical, and positioned against and using a wall of the expandable implant as a barrier.

FIG. 43 shows before-and-after, side cross-section views of a frangible gas-producing component with at least one interior, fracturable wall, enclosing two gas-producing chemicals, that causes consequential fracture of other component walls upon reaction of an initiator amount of one of the gas-producing chemicals.

FIG. 44 shows before-and-after, side cross-section views of a frangible gas-producing component illustrating a fracture that opens a passageway between chambers enclosing two reactive gas-producing chemicals.

FIG. 45 shows a close-up, side-view, cross-section of the fractured opening shown in FIG. 44.

FIG. 46 shows a side-view, cross-section of a pair of non-fracturable enclosures for the two reactive gas-producing chemicals separated by a fracturable joint of the type shown in FIGS. 44 and 45 and employing the outer implant wall as a barrier for the enclosures.

DESCRIPTION

Figure 1:
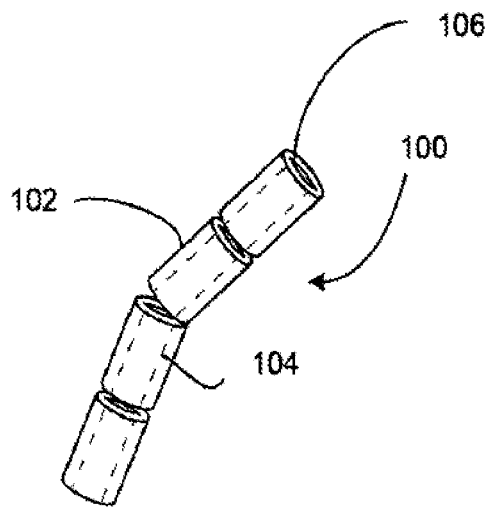
FIG. 1 shows a perspective view of one variation of structural frame members suitable for use in this implant.

Described herein are bioerodible intragastric implants that are useful in curbing appetite and that are constructed from one or more discrete expandable members. The implants may be swallowed and may be self-deployable. Also described are treatments for curbing an individual's appetite by using those devices.

The device curbs the appetite by temporarily expanding within the stomach to form a structure that contacts some portion of the stomach wall. When the implant is self-deploying, it expands in the stomach by being filled with a gas from a source that is swallowed with the device envelope or bladder. The described devices may be configured then to dissolve or to degrade after a selected period of time and be eliminated from the stomach.

The described self-deploying implant may be deployed in the stomach using, e.g., members comprising materials having "shape memory" characteristics or having significant elastic properties (e.g., elasticity or superelasticity of metals, alloys, or polymers) or other flexible constituent materials otherwise adapted to expand the device when placed in the stomach. The compositions are at least biocompatible and are desirably themselves bioerodible.

The device may comprise a single expandable member that expands upon introduction into the stomach or may comprise a plurality of discrete expandable members with attachments to other members or to a framework. Some variations of the device involve expansion of the member or members via use of an included amount of a carbon dioxide generating composition (CDGC).

Typically, the discrete expandable member of the type that is interconnected to another member is of one or more variations. In the first variation, the expandable member may be of a size and material, etc., that upon destruction of the connection to other members, it may be eliminated from the stomach without need for additional dissolution. In the other variation, the member is of a size and material in which further bioerosion is appropriate before the resultant member debris easily evacuates from the stomach.

As noted above, the various described members are desirably expandable in vivo upon contact with gastric juice. That expansion may take place over a predetermined and, perhaps extensive, period of time. The period of time during which the members erode to a size and form that passes from the stomach is similarly variable depending upon the result desired.

Expansion and dissolution times may each vary from about 0.25 hour to as much as 30 days. Obviously, the expansion times should be chosen to allow the stomach to activate the self-deploying feature of our devices before the stomach attempts to eliminate the device without deployment to the detriment of the stomach and the device.

Such predetermined time periods are to be selected by the medical specialist and reflect inter alia the size of the stomach, the age of the patient, the physical condition of the patient, food digestive parameters in the stomach and along the digestive tract, the medical condition of the stomach and its sphincters, the content of the gastric juice, and the patient's general physiological and mental condition.

The described devices are self-inflating or self-expanding and do not include external inflating valving for inflation of the implant from external sources after the implant has been deployed.

DEFINITIONS

By the term "discrete expandable member," we mean that a specific member or component is itself expandable and may be temporarily interconnected to at least one other member, perhaps a structural element or perhaps as a portion of a structural element, by a bioerodible component, e.g., a tie.

By the term "bioerodible" we mean that the material is biodegradable, digestible, or erodible or otherwise dissolvable or degradable in the stomach to a form where the material is diminished in size by chemical, biological (e.g., enzymatic), physical dissolution, solubilization, etc. to allow elimination of the material from the stomach without substantial harm.

By the term "self-inflating" we refer to a spontaneous self-inflation feature. The implant need not include any inflating valves or the like, nor external inflating means.

By the term "pasta" we refer to mixtures of carbohydrates, e.g., flour and fluids, e.g., water, possibly with a predetermined measure of proteins, especially egg-related proteins.

By the term "gelatin" we refer to a protein product derived through partial hydrolysis of the collagen extracted from skin, bones, cartilage, ligaments, etc.

By the term "about" we refer to a tolerance of ±20% of the defined measure.

Frame and Panel Structures

FIG. 1 shows a flexible biodegradable structural member (100) comprising a number of hollow tubular members (102) having passageways (104) therethrough and joined by a thread, cord, or wire (106). The thread, cord, or wire (106) may have characteristics of high elasticity, super-elasticity, or temperature shape memory allowing it to return to or form a desired shape upon being placed in the environment of the stomach. For instance, the structural member (100) may include a thread, cord, or wire (106) that includes shape memory characteristics allowing it to be compressed/twisted/folded or otherwise deformed into a small volume for introduction into the comparatively elevated temperature of the stomach and to re-form into a desired shape suitable for pressing onto the sidewalls of the stomach. The thread, cord, or wire (106) may comprise a bioerodible material or another material, as desired.

Expandable tubular members (102) may comprise a material that is expandable upon introduction into the stomach and is bioerodible to a form and size that may be eliminated from the stomach. Such materials are discussed elsewhere in a section specifically discussing those materials.

FIGS. 2A and 2B show an expanded framework (110) comprising a generally ovoid, football-shaped framework constructed from a number of structural members (100) or other similar structural members such as are discussed with relation to several of the following Figures.

FIG. 2A shows a perspective view of the expanded framework (110) where the structural members (100) are joined at a number of locations (112) to form the desired shape. Other expanded shapes may also be apparent to the knowledgeable designer, e.g., stomach shaped, cup-shaped, etc. In any event, the end sections (114) comprise rounded triangular areas (115 also shown in isolation in FIG. 2C)—the edges being defined by the structural members (100). Triangles are two-dimensional structural forms that are sturdy and support the form of the structure. In the inner two sections (116), the four-sided areas (117 also shown in isolation in FIG. 2D) may be strengthened by exterior struts (118) and interior struts (120) if so desired or needed.

The expanded form (110) shown in FIGS. 2A and 2B may be used as shown or may be used as a framework for supporting panels or the like as will be discussed below.

FIGS. 3-12 show other variations of structural members of suitable for use in the same way as is the structural member (100) shown in FIGS. 2A and 2B.

Figure 3:
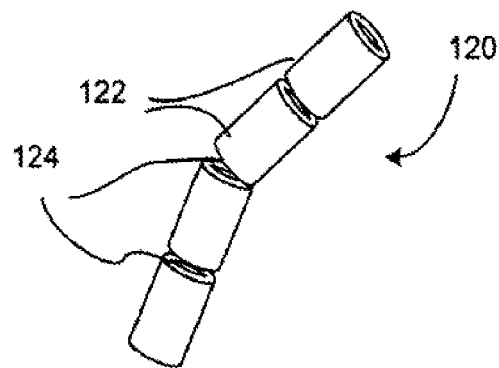

FIG. 3 shows a structural member (120) comprising a series of cylinders (122) secured to each other by ties comprising an elastomeric or rubbery material (124). As with the variation discussed with regard to FIGS. 2A and 2B, structural member (120) and the ties (124) may comprise a material that is expandable upon introduction into the stomach and is bioerodible to a form and size that may be eliminated from the stomach.

Figure 4:
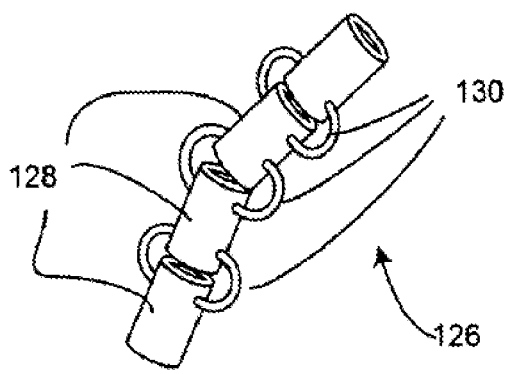

FIG. 4 shows another structural member variation (126) comprising a series of erodible expandable tubular members (128) having a thread, cord, or wire (130) extending throughout. The variation (126) also comprises several strengthening biodegradable wires (130) attached to the tubes (128) at the joints.

Figure 5:
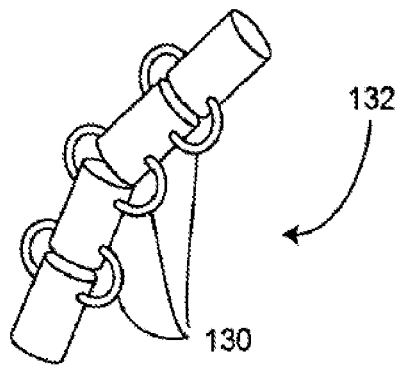

FIG. 5 illustrates another variation of the structural member (132) having strengthening biodegradable wires (130) but without the thread, cord, or wire or securing material included in the variations shown in FIGS. 1, 3, and 4.

FIG. 6 shows a variation of the structural member (136) having erodible expandable tubular members (128) but, unlike the other variations, has a coiled center member (138) linking the erodible expandable members (128). The coiled center member (138) may comprise a bioerodible material possibly having characteristics of high elasticity, super-elasticity, or temperature shape memory allowing it to return to or to form a desired shape upon being placed in the environment of the stomach.

FIG. 7 illustrates a similar variation (140) wherein the structural framework comprises a spring-like member (142) comprising one or more biodegradable materials.

FIG. 8 shows a variation (146) of the structural frame member comprising a hollow flexible biodegradable tube (148) full of gas. The tube (148) is filled with a gas upon introduction into the stomach using a self-contained gas source such as is discussed below.

FIG. 9 shows a further variation of the framework (150) having multiple spring-like members (152) interconnected using ties (154) along its longitudinal axis. The ties (154) may comprise an elastomeric or rubbery material. As discussed elsewhere, the ties (154) may comprise a material that is expandable upon introduction into the stomach and that is bioerodible to a form and size that may be eliminated from the stomach.

FIG. 10 shows a further variation of the framework (160) having sections (161) each comprising dual, substantially parallel elastic wires (162) separated by pinch-point joints (163). Again, the wires may comprise a bioerodible material. This framework variation (160) is able to be compressed or folded and to return to a desired shape upon release into the stomach.

FIG. 11 shows still a further variation (164) of the framework in FIG. 10 with sections, each section comprising dual, substantially parallel elastic wires (166) but having joints or flexible ties (168) joining the sections of wires. The ties (168) are of a material different than the wires (166).

As we discussed above, the structural frameworks shown above may be used in isolation as shown generally in FIGS. 2A and 2B. They may also be used as a support or structural frame for sheets or for inflatable envelopes or gastric balloons, as is discussed below. In any event, if the framework is used in isolation to provide pressure on the stomach wall, such a framework would be compressed, twisted, folded, or otherwise compacted or reduced to a form that may be swallowed by a patient.

The structural framework may also be characterized as ribs having ends, e.g., proximal and distal ends. Such ends may comprise sliding ends, in that they may be connected to other structural members in such a way that they slide with respect to that other member. For instance, the sliding ends may be forked or circular, with the other member situated within the open end of the fork or within the opening of the circular end. Such sliding ends may further comprise rotating hinges or a protruding element that cooperates with a slot or similar opening in the other element allowing a siding movement along the axis of that other member. Each of these ends may be used, dependent upon the design of the specific structure employed, to facilitate expansion or deployment of the implant structure in the stomach.

In some instances, the compacted form—the form of the device before it is deployed in the stomach—may be in a self-contained tension and require one or more components, denominated "shape stabilizers" to maintain that tension and to hold the compacted form in a swallowable form until reaching the stomach. The shape stabilizers may be made from materials that are bioerodible and desirably are of a form or shape that erode (and release) initially after being introduced into the stomach and therefore allow self-deployment.

Figure 12A:
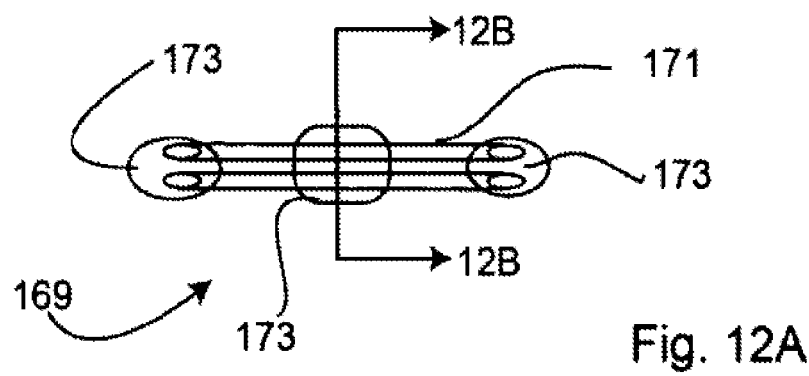
FIGS. 12A and 12B show, respectively, a side view and an end cross-section view of one variation of a folded implant comprising a structural frame member.

FIG. 12A shows a generic representation of an implant assembly (169) that has been folded and compressed into a swallowable shape and size with a framework or set of structural members (171) and having a number of shape stabilizers (173) comprising a biodegradable material, e.g., gelatin or polyglycolide, that has been applied about the framework (171) to maintain it in a compressed condition until the stabilizer or stabilizers have eroded to allow self-implantation. Such shape stabilizers may be of a variety of forms, e.g., strings, ribbons, capsules, dried hydrogels (perhaps of gelatin or polyglycolide or the like) and other bioerodible forms.

Figure 12B:
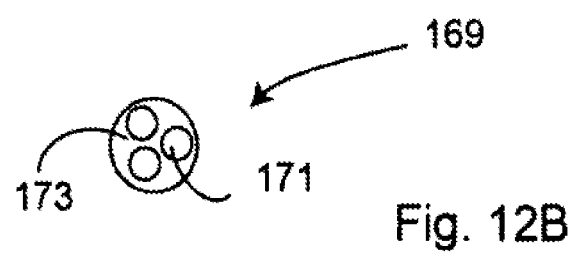

FIG. 12B shows a cross-section of the FIG. 12A device showing, in particular, the structure of the stabilizing shape stabilizer (173) about the framework members (171).

FIG. 13 shows another folded device using shape stabilizers. Specifically, FIG. 13 shows a folded framework (170) having a number of structural members (172) folded at ties (174) into a swallowable package and secured into that package by a bioerodible string or twine (176) that is looped about the package. The securing twine or string shape stabilizer (176) may optionally be tied using a "running" knot or "sack" knot. The securing twine or string (176) may be bioerodible to allow self-expansion of the folded framework (170).

Figure 14:
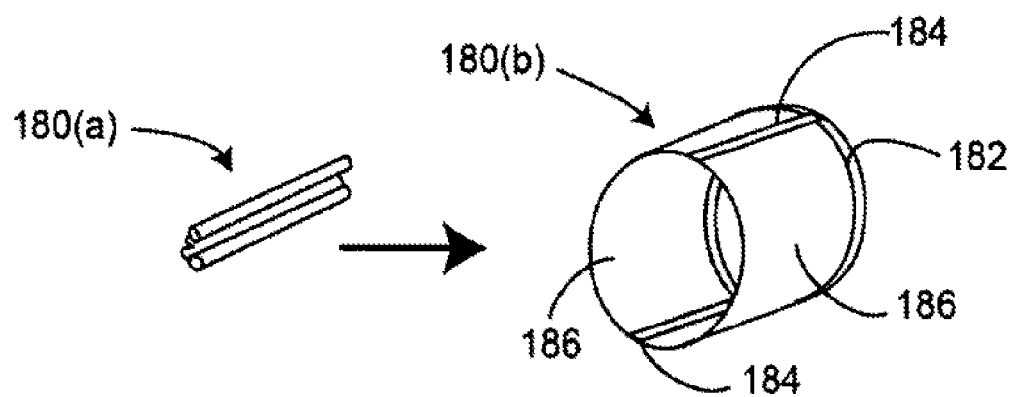
FIG. 14 shows perspective views of a folded and expanded implant comprising a structural frame member and panels.

FIG. 14 shows a generic representation of the construction of an implant (180(a) folded and ready for placement in the stomach) and that implant (180(b)) after self-deployment in the stomach. The depiction of the implant after deployment (180(b)) shows several structural members—circumferential structural members (182) and longitudinal structural members (184). Those members are connected to panels (186). Other variations of these generic structures are discussed elsewhere.

FIGS. 15A to 15F show representative cross-sections of materials that may be used in the panels or sheets mentioned elsewhere. The panels or sheets may be constructed in such a way that they are bioerodible in the stomach, bioerodible after passing through the stomach, or not bioerodible. The sheets or panels may be constructed in such a way that they have selectively erodible pathways that allow the structure to maintain its effective shape in the stomach and then to degenerate into smaller portions that may be further eroded either in the stomach or after passing out of the stomach.

FIG. 15A shows a portion of a panel (190) comprised of a bioerodible material (192) that generally is to be substantially eroded in the stomach. FIG. 15B shows a portion of a panel (194) comprised of a bioerodible material (192) that generally is to be substantially eroded in the stomach. A number of grooves (196) are included. The grooves (196) allow the panel (194) to be eroded in the stomach into smaller sections, e.g., section (198), that are non-structural in nature and may be eroded in the stomach. The grooves allow step-wise removal of the described implant from the stomach in a controlled manner.

FIG. 15C shows another panel (200) made up of a layer (202) comprised of a comparatively more erodible material, perhaps of the same class of materials used in layer (192) in FIG. 15A, and a layer (204) of a material that is in the class generally used as "enteric coatings." The enteric coating layer (204) is shown in the Figure as being on only one side; such a layer may be placed on both sides of the panel, though.

FIG. 15D shows another representative panel (206) also having a layer (208) comprised of a comparatively more erodible material, again perhaps of the same class of materials used in layer (192) in FIG. 15A, and an enteric material layer (210) having grooves (212) or other openings in the enteric coating into the more erodible material layer (208). The grooves (212) allow the panel (206) to be eroded in the stomach into smaller sections, e.g., section (211), that are non-structural in nature and may be eroded either in the stomach or after passage from the stomach. These grooves (212) also allow step-wise removal of the described implant from the stomach in a controlled manner. Again, the enteric coating layer (210) is shown in FIG. 15D as being on only one side, such a layer may be placed on both sides of the panel (206) with or without the depicted grooves.

FIG. 15E shows a representative panel (213) comprising filamentary components (215) stuck together to form an open weave material comprising one or more biodegradable materials. Such fabrics may be woven or nonwoven fabrics of filamentary materials as well.

FIG. 15F shows another representative panel (217) comprising a sheet material having protrusions (219).

In general, the panels may comprise membranes or sheets, fabrics of assembled filaments (onlays, woven, or non-woven), meshes, screens, knits, etc. The panels may be stiff or very pliable. They may be layered constructs or neat materials. They may have physical properties allowing the expanded implant to provide pressure upon the stomach wall. They may be so highly flexible that they are easily twisted or compressed into small compact packages.

Materials suitable as "enteric coatings" are provided in a separate section herein.

FIG. 16 shows a form of an implant (210) that is cup-like in shape. The form comprises four panels (212) and a bottom (214, not visible in FIG. 16). The depicted form may be considered as a schematic starting form in that it may be further compressed or folded. The panels (212) may be made of the compositions discussed above.

FIG. 17 shows a flattened form of the implant (210) shown in FIG. 16 with the side panels (212) and bottom (214). Structural members (218) around the edges of the panels (212) and a structural member (220) around the edge of the bottom panel (214) are also shown.

FIG. 18 depicts a conical implant (230) as-deployed, with a circumferential support structure member (232) and a radial support member (234). The supported panel (236) is also shown.

FIG. 19 also shows the implant (230) in the pre-formed shape having the circumferential support structure member (232), radial support member (234), and supported panel (236). The support members (232, 234) may be integrated into the panel (236) or linked to the panel (236) via tie members that may either comprise bioerodible materials or other biocompatible materials.

The conical deployed form shown in FIGS. 18 and 19 is an elected form. That is to say: the material making up the panel (236) may be "open" in the sense that it may be an "open weave" fiber material allowing fluid and solid flow through the field of the panel. The conical form allows deployment of the implant (230) in such a way that the circumferential structural member (232) rests against the stomach wall and imparts pressure against that wall providing a feeling of satiation. The "upstream" pressure of the liquids and solids inside the implant provides a continuing pressure against the circumferential structural member (232) until that member erodes sufficiently to pass from the stomach.

The radial structural member (234) provides a measure of directionality to the placement of the implant (230) in the instance where the connecting joint (238) provides some measure of rigidity to the unfolded structure of the implant (230). If radial member (234) is sufficiently long, e.g., longer than the diameter of the stomach and the connecting joint (238) is rigid (i.e., the joint sets the angle of the radial member (234) with respect to the circumferential member (232) as shown in FIG. 18) or allows the radial member (234) only a small amount of rotation with respect to the circumferential member (232), the radial member (234) acts as a "director" and tends to align the circumferential member (232) across the stomach and to press the member (232) against the stomach wall.

As a design choice, the radial member (234) may be omitted so to allow the flow resistance of the panel (236) to align the circumferential member against the stomach wall, albeit with a slower alignment rate than with a device having the radial member.

FIGS. 20A, 20B, and 20C show a truncated conical implant (240) having a smaller opening (242) and a larger opening (244). The implant (240) also includes a panel (245), larger circumferential support member (246), smaller circumferential support member (248), and longitudinal support member (250). The truncated cone shape permits passage of stomach contents through the stomach without substantial interference and yet still utilizes that flow to align the implant in the stomach, in that the modest flow resistance tends to push the large end against the stomach wall.

FIG. 20C shows a collapsed implant (240) of the type shown in FIGS. 20A and 20B with a shape stabilizer (241) ready for introduction into a patient.

FIG. 21 shows a circular implant (260) having a panel (262) and an exterior circumferential support structure (264). The circumferential support structure (264) comprises, in this variation, a series of segments (266) joined by ties (268) as discussed above with respect to FIGS. 1 and 3-5. In this instance, the panel (262) may be perforated, with one or more openings through the panel. Such a panel includes the further advantage of slowing movement through the stomach in addition to the benefit of pressing upon the stomach wall.

Central to the use and configuration of our implant is the concept that the implant size and configuration be appropriate and sufficient to provide a pressure on the stomach wall to initiate and to continue that pressure prior to its shape degradation and passage from the stomach. Several suitable expanded implant shapes are discussed above with regard to FIGS. 2A, 2B, 14, 16, 18, and 20A.

Other suitable expanded implant forms particularly useful in framework and panel constructions are shown in FIGS. 22-26C. Still other suitable forms are discussed below.

FIG. 22 shows an expanded implant form (270) having a generally half-football form comprising longitudinal structural members (272), partially circumferential structural members (274), and several panels (276). The partially circumferential structural members (274) generally provide pressure to the stomach wall.

FIG. 23 shows an expanded implant form (278) having a football-like form comprising longitudinal structural members (280), a generally central circumferential structural member (282) that may be made up of several partially circumferential members, and several panels (284). In this variation, the circumferential structural members (282) may be configured to provide pressure to the stomach wall although the various panel (284) sizes and expanded stiffnesses may be chosen to form a structure that will provide pressure on the wall.

FIG. 24 shows a truncated football expanded implant form (290) similar in overall form to the variation shown in FIG. 22 with the general exception that the small end has an opening (292) potentially with a circumferential structural member (294).

FIGS. 25A and 25B show a spiral configuration (298) of our implant comprising a biased, structural member (300) of a spinal form that tends to open when in a relaxed condition. The configuration may include one or more smaller, circular, stiffening members (302). The structural member (300) may be considered to be a spring in compression, when deployed, and is held in the depicted, stressed form by halter filament (304). The implant is shown with a columnar panel (306) that is twisted into a spiral. Another structural member (not shown) may also be employed, e.g., on the inner circumference of the spiral column and attached to the circular members, to provide additional structure to the implant.

Figure 26A:
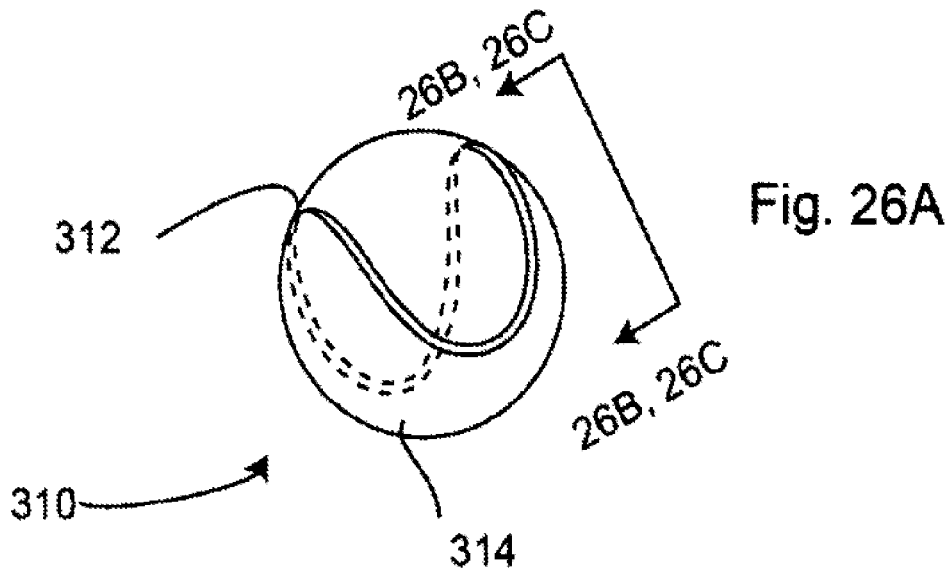
FIGS. 26A-26C show, respectively, a perspective and two side views of substantively globe-like implants.
Figure 26B:
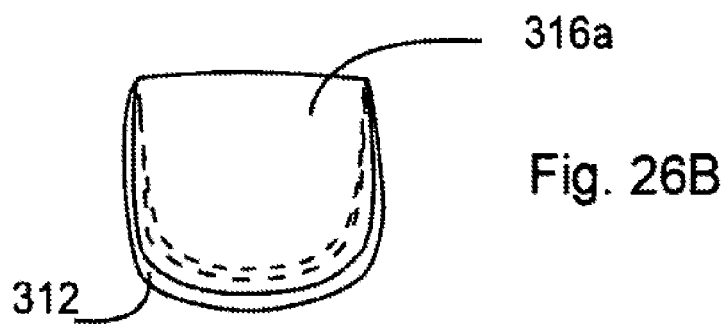
Figure 26C:
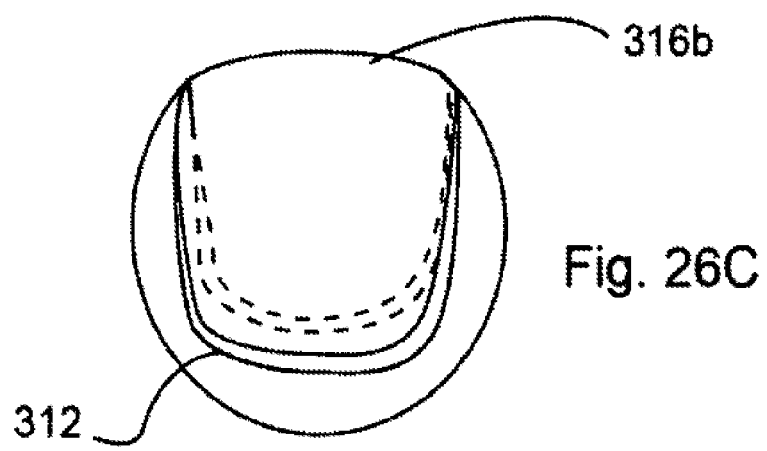

FIGS. 26A-26C show a variation of our implant (310) including a structural member that is springy (312) and that is easily twisted into smaller circular forms for introduction into the stomach. The implant (310) is shown with a generic panel (314), in perspective view, to allow overall understanding of the simplicity of the construction. FIG. 26B shows the implant with a flexible sheet for the panel (316a). FIG. 26C shows the implant with comparatively stiffer sheets for the panel (316b).

The framework system discussed above is suitable for expanding, or to aid in supporting, variously the sheet structures specifically listed above as well as self-expanding envelope structures exemplified above.

Self-Inflatable Structures Having Integral Gas Inflation Sources

Another variation of our implant comprises an efficient, self-inflating, or self-expanding implant that temporarily self-expands within the stomach of a patient using an integral gas source. Generally, when this variation of our implant is properly designed and sized, it will self-expand to a shape or to a diameter where the implant's perimeter is at least partially in contact with the interior surface of the stomach wall and thereby exerts at least a pressure on that portion of the stomach wall sufficient to trigger "fullness" responses from the stomach's nervous system. Functionally, the implant is sized to produce such a feeling in a particular patient variously before or after a patient has eaten.

After the implant has been in place in the stomach for a predetermined period of time, the implant will bioerode and pass through the stomach after being partially or completely digested. To accomplish this goal, the implant may be made from one or more bioerodible materials such as those listed herein, perhaps in combination with one or more enteric materials, again, such as those listed herein.

The expanded implant may comprise, although it need not necessarily be so, a structure having a comparatively larger size in two dimensions and a smaller size in the third direction.

When properly designed, this variation of the implant will provide a feeling of satiety, with the goals of not producing an uncomfortable feeling of fullness and without substantially changing conditions in the stomach, conditions such as temperature, digestive movements, pH, water activity ($a_w$), water availability in the stomach, and biological conditions such as the availability of digestive enzymes.

The implant self-expands due to the presence of an integral gas source. The gas source is "integral" in the sense that the components that produce the gas by chemical reaction, or biological process, or the like, are within the swallowed envelope or are in fluid communication with the envelope that forms the exterior of the expanded implant. Further, the term "integral" means that the implant's expanding gas is the product of a chemical or biological process based on gas-producing materials swallowed with the implant. The gas is neither added nor supplemented by a physical connection through a stomach opening. The integral gas source does not utilize gastric fluids as reactants in the gas source nor does the design of the implant permit the entry of gastric fluids into the interior of the un-inflated implant. External manipulation, e.g., via manual pressure or the like, may be used to initiate operation of the integral gas source in some variations, but such manipulation does not include use of any tool or means that is physically introduced into the stomach via the esophagus or via surgery. Such manipulation may, however, include the use of magnets or of applied radio-frequency energy or of physical manipulation of the swallowed implant via pressing with the hand or fingers to initiate, enhance, or continue the gas production process.

Although the gas source may, in a general sense, produce any gas that will inflate or expand the implant bladder or envelope, from a practical and safety point of view, a very good choice for such an expansion gas is carbon dioxide. The solid or liquid components suitable (and readily available) for producing carbon dioxide gas may be readily selected from materials that are themselves safe for human consumption. For instance, a suitable carbon dioxide source may comprise physically separated amounts of bicarbonate of soda and of a vinegar solution. These two materials are safe for human consumption, have no reaction products that are harmful, and are quite effective in producing carbon dioxide gas in amounts and at pressures that are useful in our implant. Only relatively small amounts of the reactants are needed to inflate the implant variation.

Chemical reactants involving simple acid-base reactions to produce carbon dioxide that are especially suitable for the gas source include: basic materials such as sodium bicarbonate ($NaHCO_3$), sodium carbonate ($Na_2CO_3$), calcium bicarbonate ($Ca(HCO_3)_3$), calcium carbonate ($CaCO_3$), and the like. Suitable acidic materials include various organic acids such as those found in vinegar (acetic acid), citrus juices (lime, lemon, orange, grapefruit juices containing citric acid), Vitamin C (ascorbic acid), tartaric acid, etc. Other organic acids, especially carboxylic acids are also useful. Carbonic acid is also operable but is, as a practical matter, too unstable at room temperatures to be a first choice for the gas source.

Figure 27A:
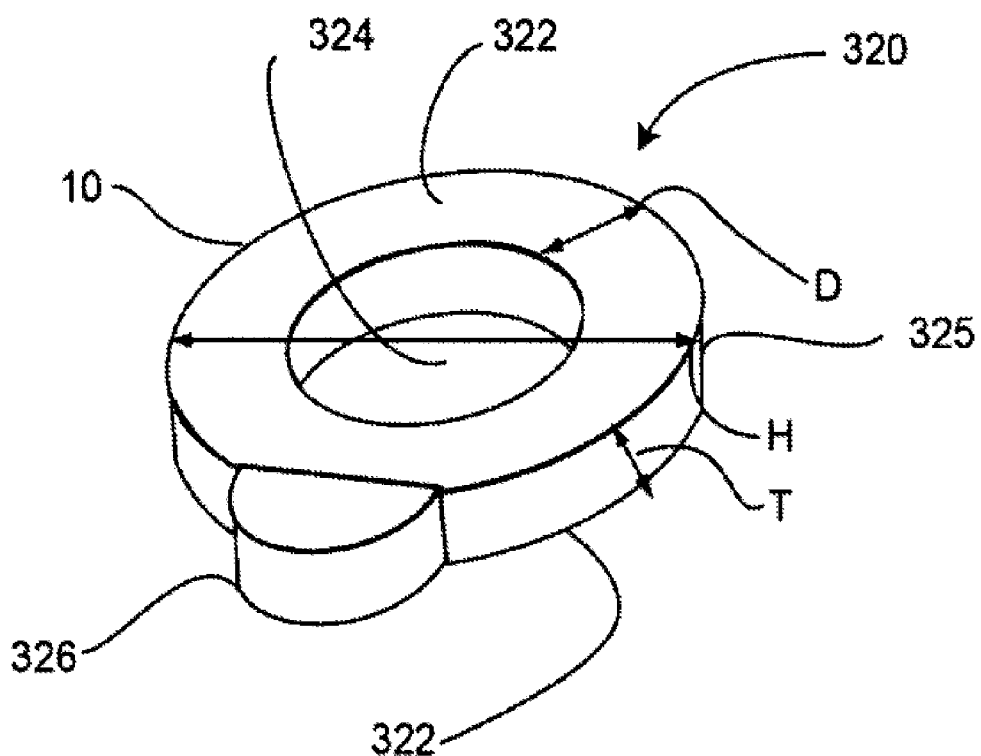
FIGS. 27A and 27B show, respectively, a perspective view and a side cross-sectional view of two related self-inflating implants.

As to the structure of this variation of our implant, FIG. 27A shows a perspective view of a flat-sided variation (320) comprising opposing, generally flat surfaces (322), an opening or passageway (324) through the implant to allow passage of stomach contents past the implant, and an outer periphery (325). The variation shown in FIG. 27A also includes a stub or extension (326) that may include one or more components of the gas source.

FIG. 27A also shows the conventions we use in describing the various dimensions of this variation of the implant (320). The dimension "H" is the diameter of the device. The dimension "T" is the thickness of the device and the dimension "D" is the difference between "H" and the diameter of the inner opening (324).

Figure 27B:
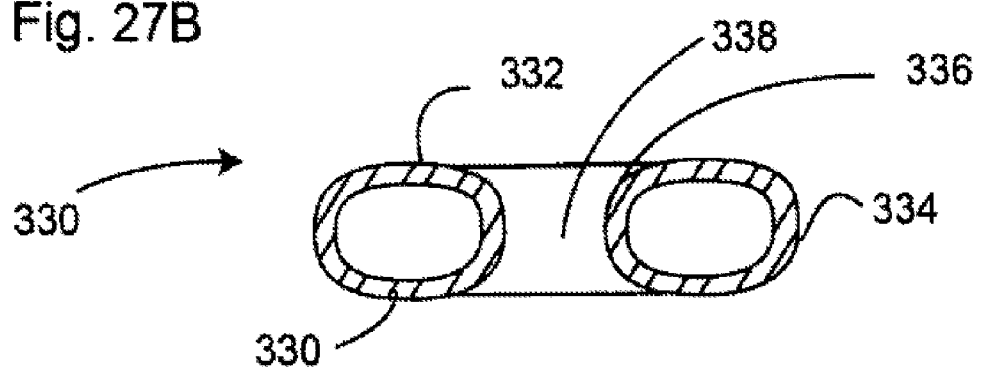

The depiction of the implant (320) shown in FIG. 27A depicts an outer periphery (325) having a relatively right-angled shoulder or edge. FIG. 27B shows a cross-section of another implant variation (330) in which the expanded form has opposing surfaces (332), an outer generally rounded periphery (334), and a rounded inner surface (336), surrounding a central opening or passageway (338). This variation (330) may be referred to as having a toroidal or donut shape.

In general, these variations of our implant, when expanded, comprise a configuration that has a generally flat shape in which D<H and T<H, the external periphery (325, 334) of which is selected to press against the sidewalls of the stomach. Typically, the "H" dimension of the expanded or inflated envelope is functionally in the range of about 75% to about 110% of the inner latitudinal diameter of the stomach, typically less than about 15 cm. The pre-inflated envelope or bladder (but not yet rolled or otherwise folded into the swallowable form) may have "T" and "D" dimensions of less, even substantially less, than about 2 cm.

The functional and physical sizes mentioned here with respect to the self-inflating implant variations of the device are, of course, based upon the implant's relationship with the size of the stomach. These sizes are also suitable for the frame-based variations discussed above.

The dimensions of such a partially or fully expanded implant may vary, e.g., the "D" dimension may be between about 0.2 and about 3.0 cm, perhaps between about 1.2 and about 1.8 cm, and perhaps between about 0.75 and about 1.5 cm; the "H" dimension typically will be between about 8 and about 18 cm, perhaps between about 11 and about 14 cm.

Depending upon the materials of construction chosen and their various thicknesses, pre-inflation collapsed implant volumes may be in the range of 0.02 $cm^3$ to about 5.0 $cm^3$ and perhaps in the range of about 1.0 $cm^3$ to about 2.0 $cm^3$. These dimensions allow the implant, when properly collapsed, to be swallowed by a patient.

Figure 28:
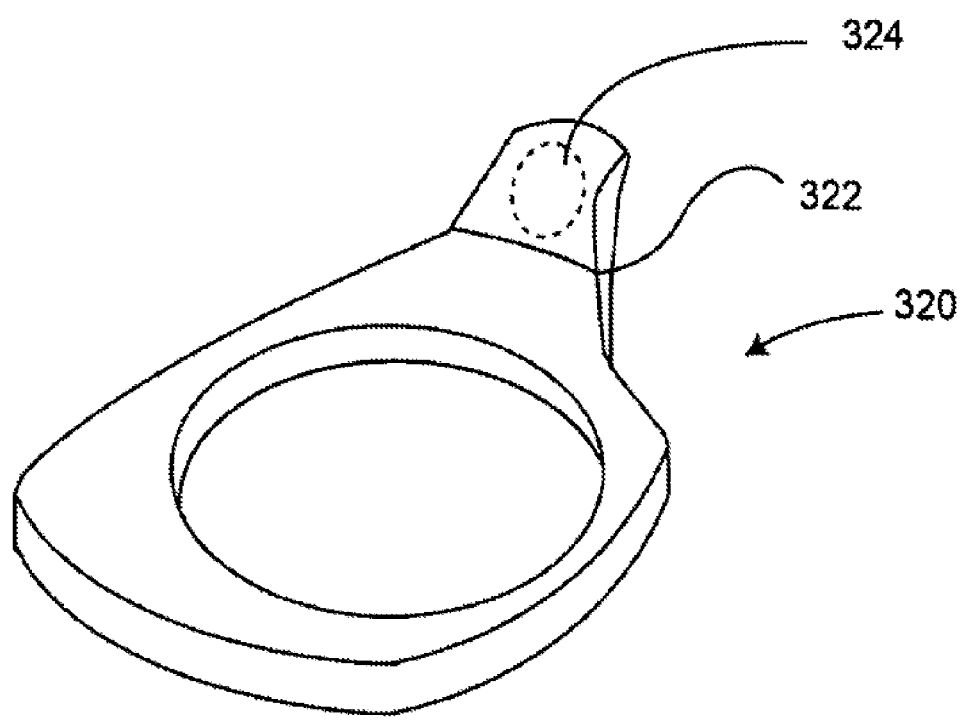
FIG. 28 is a perspective view of a variation of the implant in an uninflated configuration.

FIG. 28 provides a perspective view of the variation of our implant (320) shown in FIG. 27A, differing in that the device is in a collapsed form and has not yet self-inflated. Again, the depicted implant will yet be collapsed further so to be swallowable. Also visible in FIG. 28 is an optional fold line (322) and a component (324) of the gas generating composition discussed above. The fold line (322) may be used, if desired, to provide an added restriction preventing contact between the components of the gas generator prior to the implant's (320) unfolding in the stomach. The use of the fold line in this and certain other variations will be explained in more detail below.

Figure 29:
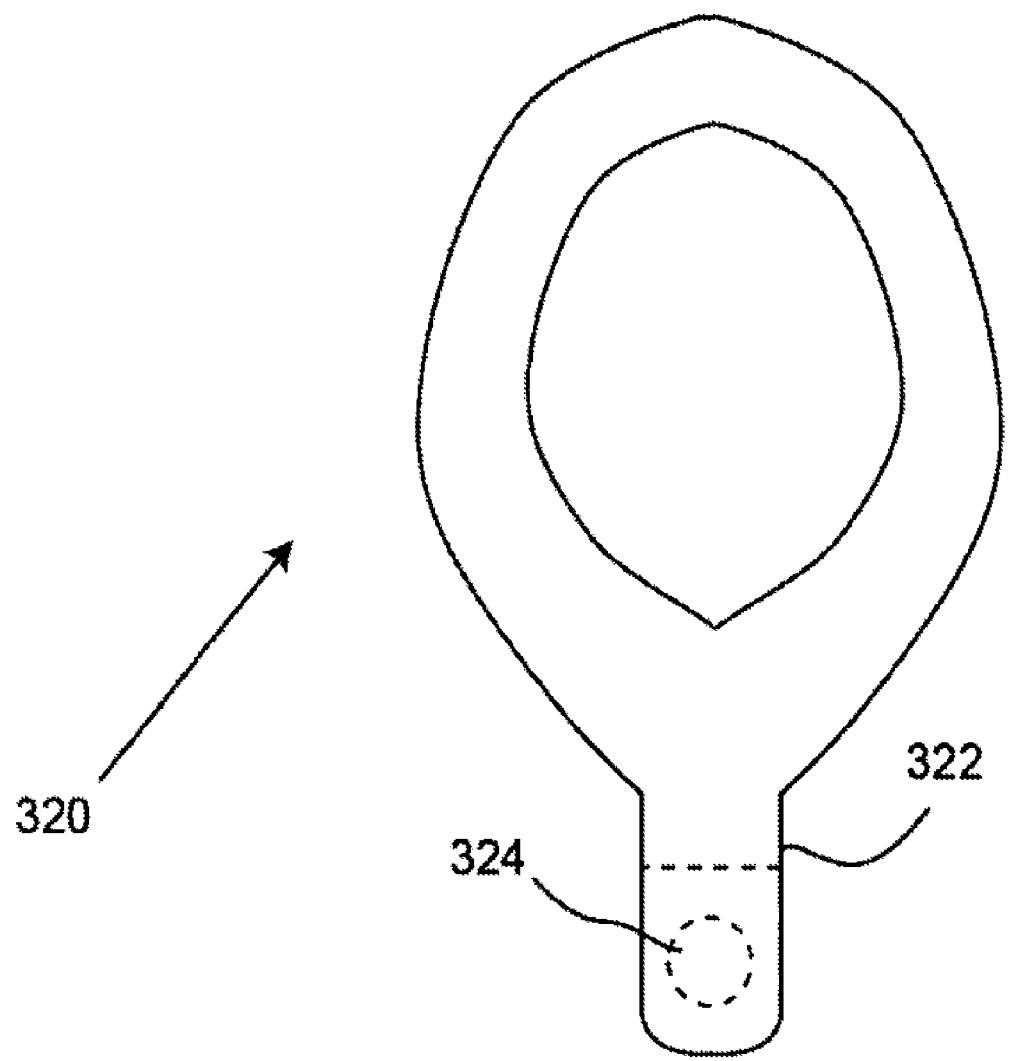
FIG. 29 is a top view of the implant variation shown in FIG. 28 after inflation or expansion.

FIG. 29 shows a top view of the expanded implant (320) otherwise shown in FIGS. 27A and 28. Fold line (322) and a component (324) of the gas generating composition as discussed above are also shown.

Figure 30:
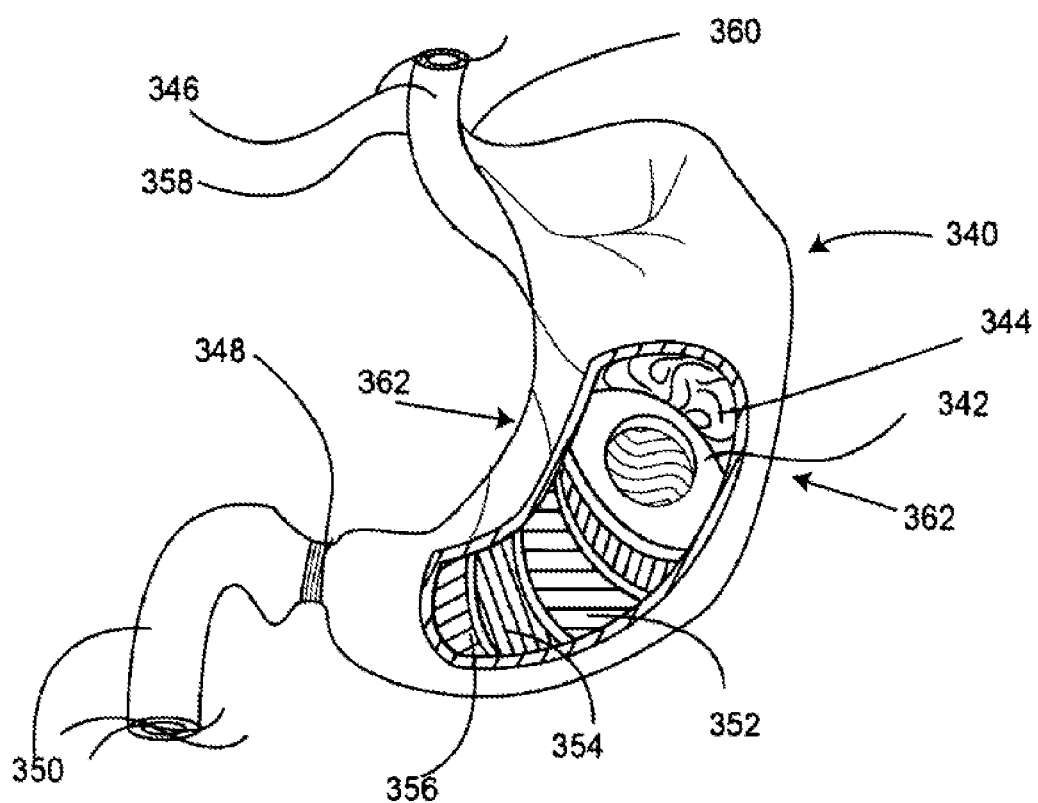
FIG. 30 is a schematic representation of an appropriate placement of our implant within the stomach.

FIG. 30 shows a partial sectional view of a stomach (340) with our self-deployed implant (342) in place against the stomach wall (344) showing the folds of the mucous membrane. Additional anatomical features of the stomach shown are the entry to the stomach (340), the esophagus (346), and the exit of the stomach (340), the pylorus (348). The pylorus (348) leads to the duodenum (350). The various layers of stomach muscle (352, 354, 356) are also shown.

The nerves in the stomach (340) are the terminal branches of the right vagus nerve (358) and the left vagus nerve (360). The right vagus nerve (358) is distributed on the back of the stomach and consequently those distributed nerve branches are not seen in FIG. 30. The left vagus nerve (360) branches on the front of the stomach (340) and those branches are depicted in FIG. 30 on the front surface of the stomach (340). A great number of branches from the celiac plexus branch of the sympathetic nerve are also distributed to the stomach. Nerve plexuses are found in the submucous coat in the stomach wall (344) and between the various muscle layers (352, 354, 356). From these plexuses, nerve fibrils are distributed to the muscular tissue (352, 354, 356) and the mucous membrane (344). The interior lateral diameter "ILD" (362) of the stomach (340) is also seen.

It is the pressure on these highly branched nerves that the implant (342) is to provide in operating to provide a feeling of satiation.

Figure 31:
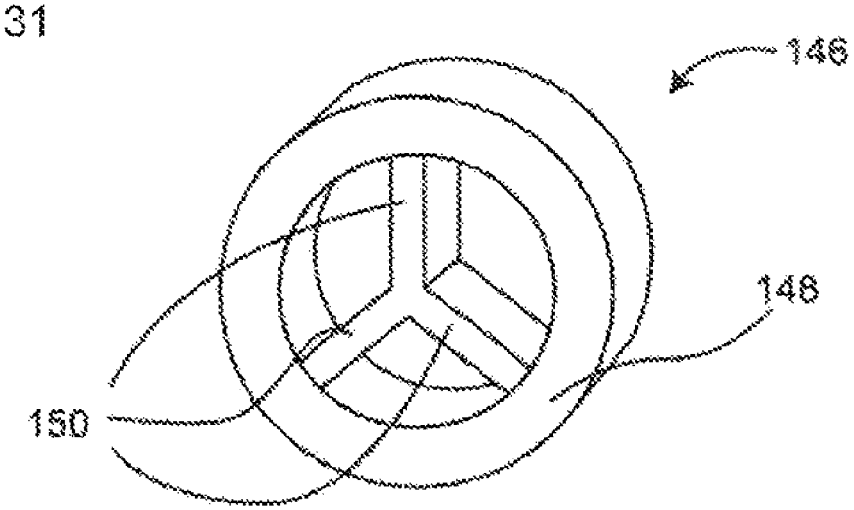
FIG. 31 is a perspective view of another variation of our implant.

FIG. 31 shows a perspective view of another variation of our self-expanding implant (370) in its expanded form. The toroidal outer shape (372) is given accentuated diametric stiffness by the three radial ribs (374).

Figure 32:
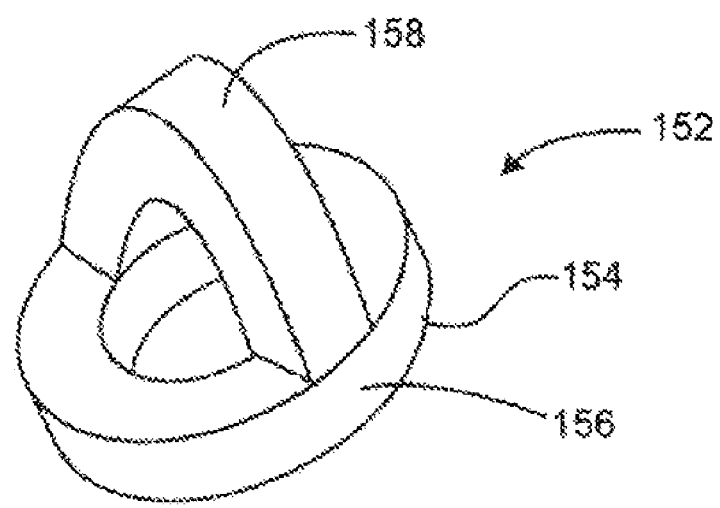
FIG. 32 is a perspective view of a variation of our implant.

FIG. 32 shows a perspective view of another variation of the self-expanding implant (376) having a flat ring or toroidal region (378), the periphery (380) of which is configured to contact the stomach wall. A half-loop (382) helps to maintain the regularity of the toroidal region (378) and is available to provide pressure against the stomach wall if the alignment of the toroidal region (378) of the implant (376) is not directly across the stomach.

FIGS. 33A-33E show a number of expandable envelope shapes that may be inflated with a modest amount of gas and by extension, using small amounts of reactants. One significant advantage of the toroidal or donut-shaped inflatable envelope discussed above is that the package to be swallowed may be made quite small and yet the exterior dimensions are comparatively extensive. That shape is able to provide a stable structure able to provide significant and widespread pressure on the stomach wall for producing the "fullness" sensation. The shapes found in FIGS. 31 and 32 and in FIGS. 33A-33E also provide such advantages.

Figure 33A:
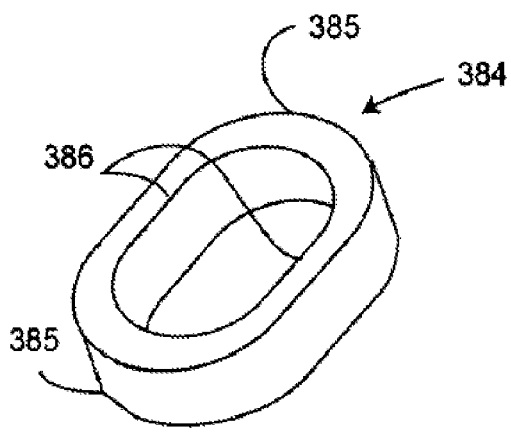

FIG. 33A shows a perspective view of an expanded implant (384) that has semi-circular ends (385) separated by two relatively straight sections (386). The rounded ends (385) provide surfaces that are broad and cover large sections of the stomach wall allowing good predictability that some portion of the stomach nervous system will be under pressure. The straight sections (386) are, in effect, structural beams that press the ends (385) against the stomach wall.

Figure 33B:
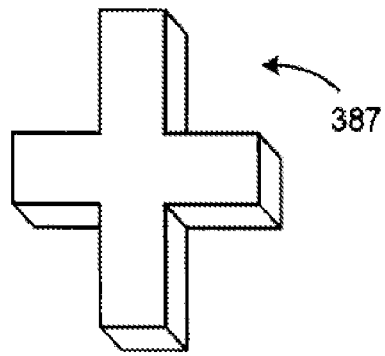

FIG. 33B shows a perspective view of an expanded implant (387) having the shape of a multiple-armed cross. The cross arms extends to press various generally opposing areas of the stomach wall. It is a sturdy structure.

Figures 1, 33C:
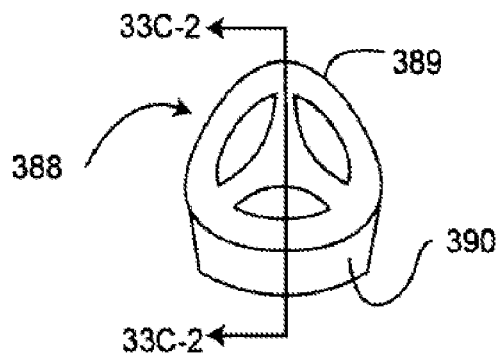
Figures 2, 33C:
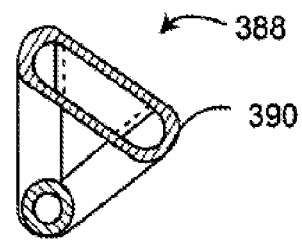

FIG. 33C-1 shows a perspective view of an expanded implant (387) having the shape of skeletal 3-pyramid. FIG. 33C-2 shows a cross-section of the FIG. 33C-1 implant. This shape is a determinate form and has rounded corners (390) for contacting the stomach wall. Because the triangle-based pyramid shape includes a determinate structure, the shape provides a variety of sites for pressing into the stomach wall.

Figure 33D:
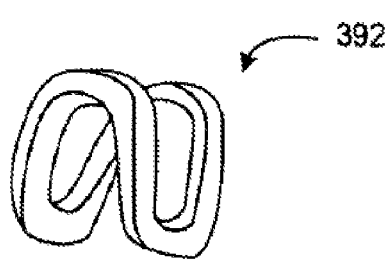
FIGS. 33D to 33E provide perspective views of two inflated variations of our implant.

FIG. 33D shows a perspective view of an expanded implant (392) having the shape of a bi-folded disc.

Figure 33E:
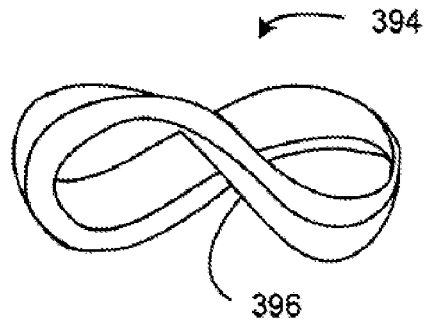

FIG. 33E shows a perspective view of an expanded implant (394) having the shape of a Moebius strip. The twist (396) in the form provides a measure of stiffness to the overall structure.

FIG. 34A provides a partial cutaway view of a hoop- or ring-shaped variation (400) of our expandable implant and further shows an alternative placement of the gas generator (402) within the hoop. This gas generator configuration is shown in FIG. 34A is further shown in the cutaway of FIG. 34B. The container or canister (402) includes two volumes (406, 408), each of the volumes containing one of the reactants, e.g., base or acid. The two reactant-containing volumes (406, 408) are separated by the wall (410). Each of the opposing, rounded walls (412, 414) includes a number of openings (416) that either allows a liquid reactant in or out. In any case, a liquid reactant present in volume (408) leaves that volume through the openings and must travel completely around the interior of torus (403 in FIG. 34A) to approach the other side of container (402) and to pass through the openings in the opposite volume (406) and initiate the reaction to produce the inflating gas. This arrangement permits ease of gas producer canister (404) installation and yet separates the reactants by a maximum path.

Figure 35:
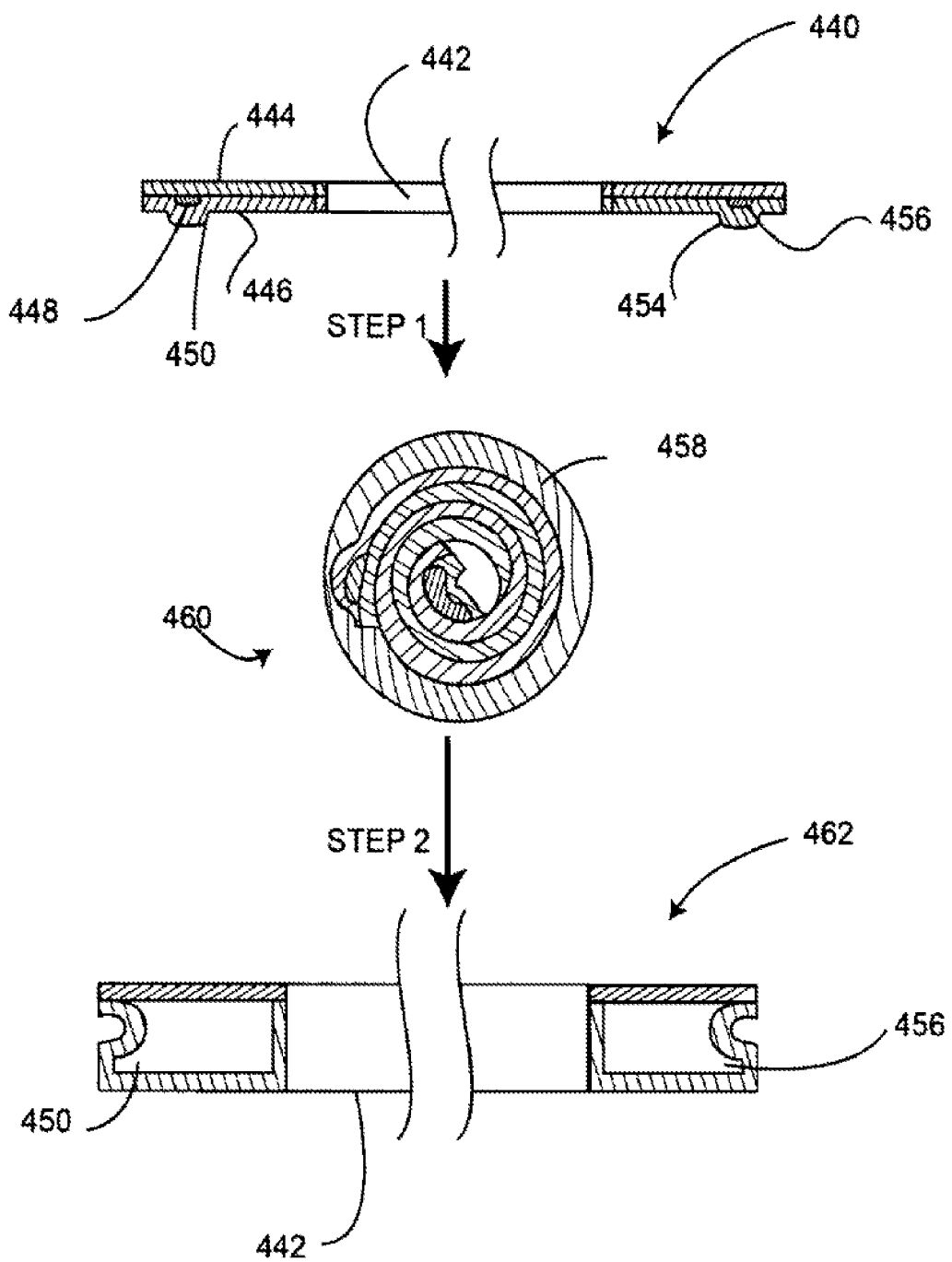
FIG. 35 shows the production of an implant that may be swallowed and the separation of the gas-producing composition components until appropriately mixed.

FIG. 35 shows a side cross-section of a self-expanding implant in three stages to demonstrate a variation for placing the two components of the gas-producing composition in isolation until appropriate for reaction and resultant gas production. Shown as the starting construction of the FIG. 35 procedure is an uninflated implant (440) having a central opening (442) with an upper flat surface (444) and a lower flat surface (446). A first component (448) is located in a first volume (450) and a second component (454) is located in the remote second volume (456).

In "Step 1," the uninflated implant (440) with the included first component (448) and the second component (454) is then rolled tightly while maintaining the isolation of the two components. The rolled implant (440) is then coated with a biodegradable material, e.g., a gelatin layer (458) to form a coated swallowable implant (460). Although the liquid may be expected to exhibit some tendency to migrate between the layers forming the upper (444) and lower surfaces through capillary action to the reactive other component, it is our experience that such occurrence is rare. The tighter the roll, the less tendency has the liquid to migrate. Although not wishing to be bound by this theory, we conjecture that any reaction that takes place through liquid seepage raises the system pressure within the rolled device and pushes the liquid back into its volume.

In "Step 2," the coated implant (460) is swallowed and the bioerodible covering (458) is dispersed allowing the tightly rolled implant to unroll and to allow the first component found in the first volume to move to and to react with the second component found in second volume (456) to form a gas, inflating the device and form an inflated implant (462).

Figure 36:
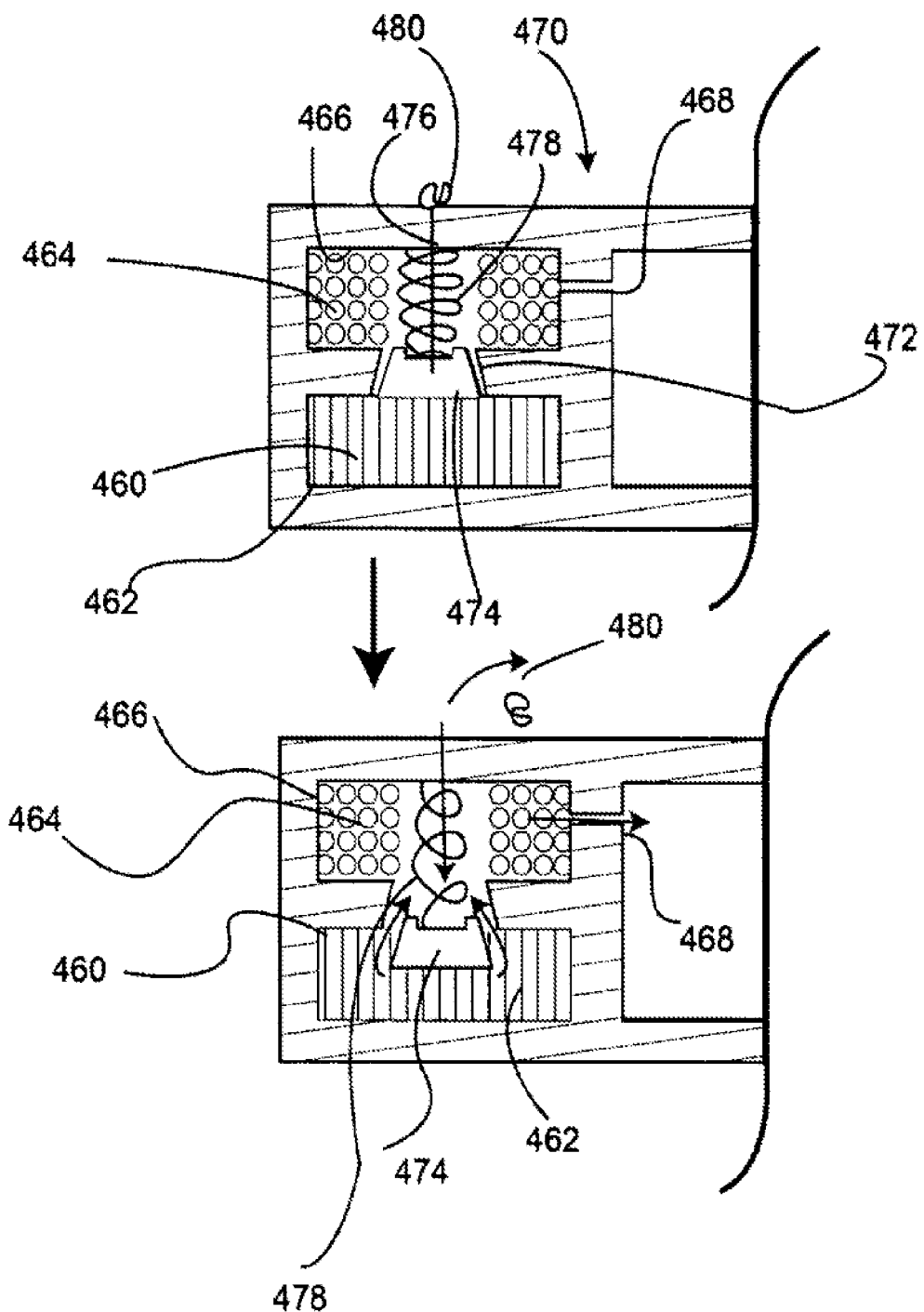
FIGS. 36-38 show side cross-sectional views of variations of valve members controllable in mixing components of the gas-producing composition.

FIG. 36 shows another schematic device for self-inflating the implant. As is the case above, at least one of the components is liquid. In this variation, a first, liquid component (460) is located in a first volume (462) potentially having a closable opening or openings only into a second volume (466) containing and a second liquid or solid component (464). The second volume (466) includes a passageway (468) into the inflatable bladder or envelope forming the implant. The first component (460) and the second component (464) together comprise the gas-producing composition.

The passageway (472) between the first volume (462) and the second volume (466) is temporarily closed using a plug (474) that is held in a closed position using a thread (476). Spring (478) pushes upon plug (474) and thereby biases the plug (474) to open. Thread (476) pulls against the spring. If thread were not there, as is the case in the lower panel of FIG. 36, the spring (478) compression would open the plug (474).

Exterior to the implant is a digestible knot (480) or the like that, once digested or eroded in the stomach as shown in the lower panel of FIG. 36, allows the thread (478) to slip through the upper wall and, in turn, allows the spring (474) to push the plug (474) into the first volume (462) and displace some of the first liquid component (460) into the second component (464) in second volume (466) producing inflating gas that escapes through opening (468) to inflate the implant (470). The spring (474) may be formed of a biodegradable polymer such as polyglycolic acid.

Figure 37:
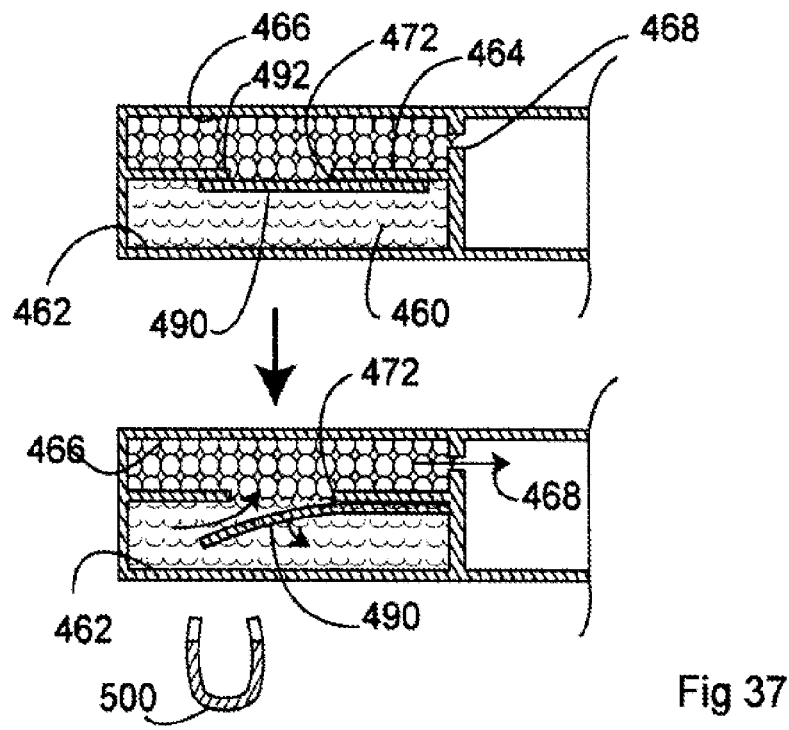

FIG. 37 shows a generally similar arrangement to that of FIG. 36, but with a different sealing or valving arrangement. In this variation, the passageway (472) between the first volume (462) and the second volume (466) is temporarily closed using a flexible, polymeric, magnetic flapper (490) optionally having a magnetic seat (492) surrounding opening (472).

The flapper (490) may comprise a polymeric, flexible material including, for instance, ferromagnetic particles. The ferromagnetic particle loading should be sufficient to allow a magnet (500) move the flapper (490) away from opening (472) as shown in the lower panel of FIG. 37 and to allow fluid (460) from first volume (462) into second volume (466) for reaction to gas ultimately flowing through opening (468) to inflate the implant. In practical operation, a magnet could be applied to a patient's stomach area to open flapper (490) and initiate gas production.

Figure 38:
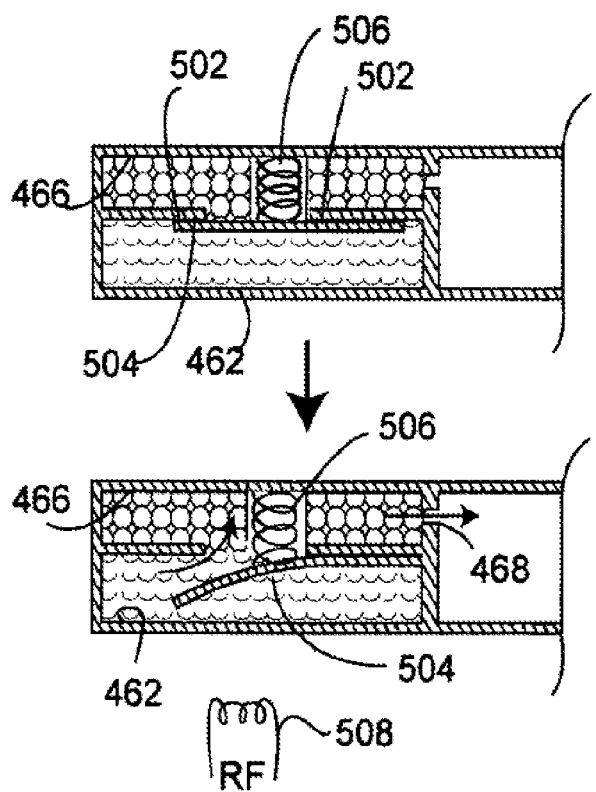

FIG. 38 shows still a similar arrangement to that shown in FIG. 37 but instead utilizing a thermoplastic sealant (502) to hold flapper (504) in place against a spring (506) in compression until released by application of radiofrequency energy (508) to melt the thermoplastic sealant (502) and to allow fluid (460) from first volume (462) into second volume (466) for reaction to gas ultimately flowing through opening (468) to inflate the implant. Desirably such a thermoplastic sealant (502) would have a fairly low softening point and be loaded with a material such as ferromagnetic or ferrimagnetic particles that tend to concentrate the RF energy into the sealant for softening.

Figure 39:
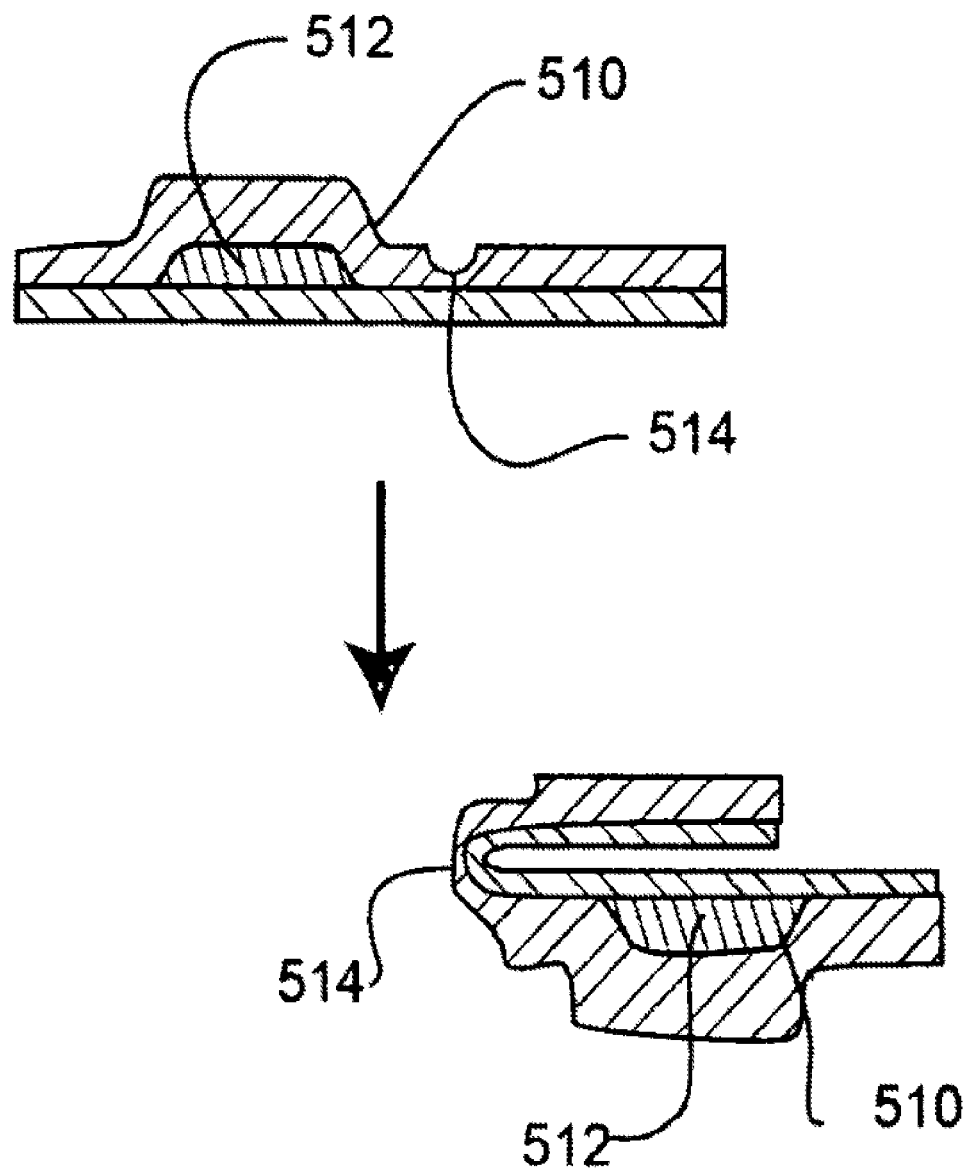
FIG. 39 shows a side cross-sectional view of a folded member for controlling the isolation of components of the gas-producing composition.

FIG. 39 simply shows a volume (510) that contains one of the components (512) of the gas-producing composition and the presence of a fold line (514) to concentrate sealing forces at that line (514) when folded (as shown in the lower panel of FIG. 39) and to maintain the isolation of the component (512) within volume (510).

The folded construct may simply be folded, as is, into a roll such as found in Step 2 of FIG. 35 to help maintain isolation of reactants until needed for gas expansion.

Another set of structures suitable for maintaining separation between the components of the gas-producing composition are those we characterize as "frangible" structures. By "frangible" structures, we mean those structures that maintain separation between the two components until some exterior movement or pressure causes a physical fracture of at least some portion of the structure permitting contact between and consequent chemical reaction between the components of the gas-producing composition. As is the case with each of the gas-producing compositions discussed above, either or both of the components may be in a liquid, solid, semisolid, or gel form.

The impetus for physically fracturing some portion of the frangible structure may be any intracorporal movement or pressure, natural or applied. Pressures such as those caused as a result of peristaltic motion or the act of swallowing or physical pressure applied from outside the body (e.g., due to a health professional pressing on the stomach) may be used to fracture the fracturable component of the frangible structure. Movements such as that involved with unfolding the balloon after dissolution of the outer capsule, peristaltic motion, or physical manipulation of the frangible structure may be used to fracture the fracturable component of the frangible structure.

The region of fracture may be widespread, e.g., destruction of a structural wall in the frangible structure, or narrow, e.g., the opening of a small passageway or hole allowing contact between the gas-producing chemicals. The relative size of the region of fracture may be between these extremes.

A wide variety of materials are suitable for use in the fracturable component of the frangible structure. Waxes such as petroleum waxes, bees wax, polyethylene waxes, are suitable. Natural materials (or those derived from natural materials) such as hard gelatins, rice and wheat noodle materials, starch-based compositions perhaps comprising potato-starch with or without synthetic and natural polymers, may be used as some portion of the fracturable components. The fracturable component may comprise regions of non-fracturable materials (perhaps dissolvable in stomach fluids such as polyglycolic acid membranes) edged by fracturable materials.

FIGS. 40A-40C show side-view cross-sections of three frangible structures having outer fracturable coverings. FIG. 40A shows a generally square-cornered structure (600) having an outer fracturable cover (602) and containing one or the other of the gas-producing chemicals. FIG. 40B shows a structure (606) having a parallelogram cross-section that, because of its non-right-angle corners, will fracture under pressure more easily than will the structure shown in FIG. 40A. FIG. 40C shows a structure (610) with regions (612) that provide ease of stress-fracture. The hillocks (612) need not have the specific shape shown there to achieve enhanced fracturably. Other shapes have stress-concentrating abilities.

FIGS. 41A-41C show structures in which one or more fracturable surfaces are used to maintain a separation between the gas-producing components. FIG. 41A shows a frangible structure (614) having two fracturable surfaces or walls (616) and a central wall (618), all combining to enclose a first gas-producing solid or fluid (620) and a second gas-producing solid or fluid (622). The central wall (618) may be fracturable or not. FIG. 41B shows a frangible structure (624) in which a fracturable central wall (626) is used to separate a first gas-producing solid or fluid (620) and a second gas-producing solid or fluid (622). FIG. 41C shows a frangible structure (627) having an outer surface or wall (628) and central wall (630) used to separate a first gas-producing solid or fluid (620) and a second gas-producing solid or fluid (622).

The structures shown in FIGS. 40A-40C and 41A-41C might be introduced into the expandable bladder, balloon, or envelope but not necessarily affixed to the interior of the envelope or balloon.

FIG. 42 shows a frangible structure (640) in which a fracturable wall (642) contains one of the first or second gas-producing solid or fluid (644) in conjunction with a portion of the expandable envelope (646). Two (or more) of these fracturable walls may be used in a single expandable envelope to enclose selected amounts of the first or second gas-producing solid or fluids. The multiple structures need not be all of the same size.

FIG. 43 shows before-and-after, cross-section, side-views of a frangible structure (650) having at least one interior fracturable wall (652). The overall structure of the device (650) includes three containment volumes or regions (654, 656, 658). The small volume (654) is isolated from the adjacent chamber (656) by fracturable wall (654) and contains either of an acid or a base. The adjacent or middle chamber (656) contains acid (if the small chamber (654) contains base) or a base (if the small chamber (654) contains an acid). The final chamber (658) contains an acid or base as is found in the small chamber (654).

This structure helps to enhance the mixing of the reactants. When the fracturable wall (652) breaks, as shown in part (b) of FIG. 43, the small amount of reactant in volume (654) reacts with the complementary reactant in chamber (656) to form a gas and that expansion pushes the reactant in middle chamber (656) through a thin wall (660) between chamber (656) and chamber (658)) and into the end chamber (658) to cause reaction of the reactant in chamber (656) and that in chamber (658) and to form the larger bulk of gas. The expansion of the gas will force through thinned end wall (662) into the outer envelope for expansion of that envelope.

One or more of thin walls (660, 662) may be fracturable regions, if so desired.

FIG. 44 shows before-and-after, cross-section, side-views of a frangible structure (670) having at least one interior fracturable joint (672) separating two volumes (674, 676) containing the two gas-producing chemicals. Bending the fracturable joint (672), as seen in portion (b) of FIG. 44, both opens the passageways to the two volumes (674, 676) and opens the joint to the interior of the expandable envelope. FIG. 45 shows a close-up side view of the fracturable joint (672) found in the device of FIG. 44. These types of frangible seals have been used extensively. See, for instance, U.S. Pat. No. 4,790,429, to Fukushima.

Finally, FIG. 46 shows a frangible structure (680) in which a pair of walls (682, 684), adherent to the envelope wall (686), each define a volume (688, 690) containing one of the first or second gas-producing solid or fluid (692, 694). The walls are joined at a fracturable joint (696) of the type described in conjunction with FIGS. 44 and 45. Fracture of the fracturable joint (696) allows contact of the reactant gas-producing chemicals and expansion of the envelope.

Methods of Use

The described implant is used in the following fashion: the swallowable device is (a) administered orally to the patient in a collapsed configuration, (b) transported to the stomach, (c) expanded in the stomach to an approximate predetermined size providing pressure on the stomach wall, perhaps by expansion of an expandable member or upon erosion of a shape stabilizer, (d) disassembled after a predetermined period of time by bioerosion and (e) evacuated from the stomach.

The described devices may be used to curb appetite. This treatment comprises the step of periodic oral administration of biodegradable self-inflating intragastric implant constructed from one or more discrete expandable members. The intervals between each administration are determined by a medical professional after taking into account the physiological and mental characteristics of the patient. This treatment is especially useful wherein the deflated implant is swallowed before meals such that the food intake during the meal and afterwards is decreased.

Biodegradable Polymers

Bioerodible or biodegradable polymers include, without limitation, biocompatible polymers that are may be bioerodible by cellular action or are biodegradable by action of body fluid components, such as those found in gastric juices. Such polymeric substances include polyesters, polyamides, polypeptides, polysaccharides, and the like. Suitable biocompatible, biodegradable polymers, include polylactides, polyglycolides, polycaprolactones, polyanhydrides, polyamides, polyurethanes, polyesteramides, polyorthoesters, polydioxanones, polyacetals, polyketals, polycarbonates, polyorthocarbonates, polyphosphazenes, polyhydroxybutyrates, polyhydroxyvalerates, polyalkylene oxalates, polyalkylene succinates, polymalic acid, poly(amino acids), polymethyl vinyl ether, polymaleic anhydride, chitin, chitosan, and their block and intimate copolymers, terpolymers, or higher polymer-monomer polymers and combinations and mixtures thereof. Many of the more operable biodegradable polymers are degraded by hydrolysis.

These polymers may be either surface erodible polymers such as polyanhydrides or bulk erodible polymers such as polyorthoesters. Poly(1-lactic acid) (P1LA), poly(dl-lactic acid) (PLA), poly(glycolic acid) (PGA), polycaprolactones, copolymers, terpolymer, higher poly-monomer polymers thereof, or combinations or mixtures thereof are very useful biocompatible, biodegradable polymers. One very useful biodegradable copolymer comprises a lactic acid and glycolic acid copolymers sometimes referred to as poly(dl-lactic-co-glycolic acid) (PLG). The co-monomer (lactide:glycolide) ratios of the poly(DL-lactic-co-glycolic acid) commercial materials are typically between about 100:0 to about 50:50 lactic acid to glycolic acid. Co-monomer ratios between about 85:15 and about 50:50 lactic acid to glycolic acid are quite suitable. Blends of PLA with PLG, e.g., between about 85:15 and about 50:50 PLG to PLA, are also used to prepare suitable polymer materials.

PLA, P1LA, PGA, PLG, their combinations, mixtures, alloys, and blends are among the synthetic polymers approved for human clinical use. They are used as surgical suture materials and in various controlled release devices. They are biocompatible and their degradation products comprise low molecular weight compounds, such as lactic acid and glycolic acid, which enter into normal metabolic pathways. Furthermore, copolymers of poly(lactic-co-glycolic acid) offer the advantage of a large spectrum of degradation rates, the time-to-failure of a selected filament ranging from a few days to years by simply varying the copolymer ratio of lactic acid to glycolic acid.

To enhance bio-degradation of the biodegradable polymers listed above, those polymeric compositions may also include enzymes chosen to facilitate the biodegradation of those polymers. Suitable enzymes and similar reagents are proteases or hydrolases with ester-hydrolyzing capabilities. Such enzymes include proteinase K, bromelaine, pronase E, cellulase, dextranase, elastase, plasmin streptokinase, trypsin, chymotrypsin, papain, chymopapain, collagenase, subtilisn, chlostridopeptidase A, ficin, carboxypeptidase A, pectinase, pectinesterase, various oxidoreductases, various oxidases, and the like. The inclusion of an appropriate amount of such a degradation enhancing agent may be used to regulate implant erosion time.

Enteric Coating Materials

Enteric coating materials suitable for use in our device may be selected from known aqueous enteric film coating systems, such as aqueous dispersions of acrylic resins, especially, polymethacryl methacrylate copolymers, and dispersions of acetates, especially, cellulose acetate phthalate polymers. Suitable members include acrylic-based resins, azopolymers, polymers of polyvinylacetate and polyacrylic acid, copolymers of methacrylic acid and methylmethacrylate, methylcellulose, carboxymethylcellulose, hydroxypropylcellulose, and hydroxypropylmethylcellulose, polyvinyl acetyldiethylaminoacetate, cellulose acetatephthalate and ethyl cellulose, and copolymers of methacrylic acid and methyl methacrylate. Adjuvants such as shellac, talc, stearic acid, and a plasticizer may also be included. Suitable compositions may be obtained by esterifying a carboxyalkyl group of carboxyalkyl cellulose, such group selected from hydroxypropylmethylcellulose (HPMC), hydroxypropylcellulose (HPC), carboxymethylcellulose, and sodium or calcium salts thereof; carraginan, anginic acid, and magnesium, sodium, and calcium salts thereof; povidone, polyvinylalcohol, tragacanth gum, chitosan, and chitin; elastic polymers, rubbers, bio-rubbers, or silicones; poly(glycerol sebacate) and/or its derivatives; fluoropolymers such as polytetrafluoroethylene (PTFE), ePTFE, and fluorinated ethylene-propylene resins (FEP); polyethylene terephthalate (PET); Hytrel polyesters; various aromatic polymers, and certain forms of polyethereketone (PEEK); various of the Nylons, especially Nylon 12; biodegradable and bioabsorbable elastomers such as hydrogels, elastin-like peptides, poly hydroxyalkanoates (PHA's), and biodegradable polymers such as poly(lactide), poly (glycolide), and their copolymers (PLGA); alginate and sodium alginate, polyethylene glycol and its derivatives.

Other suitable materials include hydrogels, acetal copolymers and homopolymers. Acrylonitrile butadiene styrene (ABS) and mixtures of ABS with polycarbonates, polyamides, polyimides, polyacrylates, polyaryl sulfone, polycarbonates, polyetherimide, polyether sulfone, polyphenylene oxide, polyphenylene sulfide, polypropylene, polysulfone, polyurethane, polyvinyl chloride, and styrene acrylonitrile are suitable. Various materials such as animal-originated intestine, bowels or the like, starch, pasta, pre-gelatinized starch, lactose, mannitol, sorbitol, sucrose, and dextrin are suitable. Other approved materials such as Carbomer 910, 934, 934P, 940, 941, or 1342, calcium carbonate, calcium phosphate dibasic or tribasic, calcium sulfate, and talc. Amine-based polymers such as poly(allylamine hydrochloride) crosslinked with epichorohydrin arid alkylated with 1-bromodecane and (6-bromohexyl)-trimethylammonium bromide; polymers that are made by polymerizing an aliphatic amine monomer, e.g., a saturated or unsaturated, straight-chained, branched or cyclic non-aromatic hydrocarbon having an amino substituent and optionally one or more additional substituents.

Metallic Bioerodible Materials

Metallic bioerodible materials include the metals magnesium, titanium, zirconium, niobium, tantalum, and zinc. Silicon is a bioerodible semi-metal. Mixtures and alloys of these materials are also bioerodible, e.g., certain zinc-titanium alloys, for example, as discussed in U.S. Pat. No. 6,287,332, to Bolz et al.

The physical properties of such alloys may be controlled both by selection of the metal and by selecting the relative amounts of the resulting alloy. For example, addition of about 0.1% to 1% weight of titanium reduces the brittleness of crystalline zinc. The addition of gold to the zinc-titanium alloy at a weight percentage by weight of 0.1% to 2% reduces the alloy's grain size and raises the tensile strength of the material.

Other bioerodible metallic alloys include the materials discussed just above and one or more metals selected from lithium, sodium, potassium, calcium, iron, and manganese. The materials from the first group may form an oxidic coating that is somewhat resistive to erosion upon exposure to gastric fluids. The metals from the second group are comparatively more erodible in gastric fluids and promote the dissolution of the otherwise resistive coating.

Further details relating to the latter alloys are also found in U.S. Pat. No. 6,287,332 to Bolz et al., which is incorporated herein by reference in its entirety.

Magnesium alloys are particularly suitable members of this class. The alloys, for instance, may comprise an alloy of lithium and magnesium with a magnesium-lithium ratio of about 60:40, optionally containing fatigue-improving components such as zinc. Sodium-magnesium alloys are also suitable.

Adjuvant Compositions

The body of the implant may also comprise adjuvant compositions such as may be selected from therapeutic compositions, slow-release therapeutic compositions, medications, pH buffers, anti-acid compositions, anti-inflammatory agents, antihistamines, additives, lubricants, uv contrasting agents, ultrasound contrast agents, radio-opacifiers, diagnostic agents, digestive-related therapeutic agents, probiotic bacteria cultures or any combination thereof. Depending upon the adjuvant composition and the material in the implant body, the adjuvant may be infused into, mixed with, or coated onto the implant body.

We claim:

1. A method for curbing appetite in a patient comprising steps of:
   a. introducing a compacted, swallowable, self-expanding, temporary gastric implant into a stomach of the patient; and
   b. inflating the gastric implant, when in the stomach, to a predetermined size and shape; thereby creating a feeling of fullness and curbing the appetite;
   wherein the inflating of step (b) is affected by the presence of the implant in the stomach of the patient, wherein the gastric implant is selected from the group consisting of:

a. a gastric implant comprising:
   i. at least one expandable envelope having an interior and an exterior, the envelope configured to seal temporarily, after the implant has been swallowed by the patient, the interior of the envelope from gastric fluid in the stomach at least until an integral, frangible gas-producing composition in fluid communication with the interior of the envelope produces a gas to expand the envelope to a pre-selected size, the envelope, when expanded, contacts walls of the stomach sufficiently to produce a sensation of fullness in the stomach; and wherein the envelope is operable to maintain expansion for the pre-selected period of time and,
   ii. an integral, frangible gas-producing composition configured to produce a gas after being swallowed by the patient and upon fracture of at least a portion of the integral, frangible gas-producing composition; and,
b. a gastric implant comprising:
   i. at least one expandable envelope including at least one bioerodible material, the envelope having an interior and an exterior, a toric shape upon expansion, and a pre-selected diameter that, upon expansion, contacts walls of the stomach sufficiently to produce a sensation of fullness in the stomach, the envelope operable to maintain expansion for a pre-selected period of time;
   ii. a gas-producing composition operable to produce carbon dioxide gas for expansion of the at least one expandable envelope after being swallowed by the patient, the expansion affected by the presence of the implant in the stomach, and,
   iii. an enclosure including a bioerodible material, the enclosure enclosing the expandable envelope and gas-producing composition prior to expansion, and having a size suitable for swallowing by the patient; and
   wherein the gastric implant comprises:
   a. a plurality of discrete expandable elements; and,
   b. attaching means adapted to attach each of the discrete expandable elements to at least one other discrete expandable element.

2. The method according to claim 1, wherein the introducing of step (a) further comprises swallowing of the gastric implant by the patient.

3. The method according to claim 1, wherein the introducing of step (a) further comprises endoscopically implanting the gastric implant into the stomach of the patient.

4. The method according to claim 1, wherein the inflating of step (b) further comprises contacting at least part of the gastric implant with at least part of an interior wall of the stomach, wherein the contacting creates a feeling of fullness, thereby curbing the appetite of the patient.

5. The method according to claim 1, wherein the gas produced is carbon dioxide.

6. The method according to claim 1, wherein the gas-producing composition comprises a base and an acid.

7. The method according to claim 6, wherein (a) the base is selected from the group consisting of sodium bicarbonate ($NaHCO_3$), sodium carbonate ($Na_2CO_3$), calcium bicarbonate ($Ca(HCO_3)_2$), calcium carbonate ($CaCO_3$), and mixtures thereof, and (b) the acid is selected from the group consisting of vinegar, acetic acid, citrus juices selected from the group consisting of lime, lemon, orange, and grapefruit juices and their mixtures, ascorbic acid, tartaric acid, and mixtures thereof.

8. The method according to claim 1, wherein the integral, frangible gas-producing composition comprises a base and an acid, and further comprises at least one fracturable region that at least partially contains at least one of the base and the acid, the fracturable region configured to allow contact of the base and the acid upon fracture of the fracturable region after the swallowing by the patient.

9. The method according to claim 8, wherein the at least one fracturable region comprises at least one fracturable wall that at least partially contains at least one of the base and the acid.

10. The method according to claim 9, wherein the at least one fracturable wall wholly contains one of the base and the acid.

11. The method according to claim 9, comprising more than one fracturable wall containing the base and the acid.

12. The method according to claim 9, wherein the at least one fracturable wall and the expandable envelope in combination comprise at least one of the base and the acid.

13. The method according to claim 9, wherein the at least one fracturable wall comprises more than one fracturable wall that in combination with the expandable envelope contain the base and the acid.

14. The method according to claim 8, wherein the at least one fracturable region comprises at least one fracturable joint, the fracturable joint allowing contact of the base and the acid upon fracture of the at least one fracturable joint after the swallowing by the patient.

15. The method according to claim 8, wherein the at least one of the base and the acid is partially contained by the expandable envelope.

16. The method according to claim 1, wherein the inflating of step (b) further includes inflating the gastric implant to a shape that allows continued passage of material through the stomach while the implant is inflated.

17. The method according to claim 1, wherein the inflating of step (b) further includes inflating the gastric implant to a shape selected from the group consisting of toric, X-shaped, Plus-shaped, ovoid, truncated ovoid, half-football shaped, toroid, bridged toroid, ring-shaped, spiral, Moebius strip, cylindrical, conical, truncated conical, cup-shaped, multiple-armed cross, skeletal pyramidal, double flexed washer, and stomach-shaped.

18. The method according to claim 1, wherein the inflating of step (b) further includes inflating each of the plurality of discrete expandable elements according to a predetermined sequence.

19. The method according to claim 1, wherein the inflating of step (b) further includes inflating each of the plurality of discrete expandable elements at a predetermined time of between about 0.25 hour and about 30 days from a time that the implant reaches the stomach.

20. The method according to claim 1, further comprising a step (c) of disassembling the gastric implant.

21. The method according to claim 1, further comprising a step (c) of disassembling the gastric implant by:
   i. disassembling each of the discrete expandable elements individually;
   ii. detaching the discrete expandable elements from the attachment means individually, and
   iii. evacuating the gastric implant from the stomach of the patient, wherein the evacuating includes evacuating each of the discrete expandable elements individually from the stomach.

22. The method according to claim 21, further comprising bioeroding and deflating each discrete expandable element prior to evacuation from the stomach.

23. The method according to claim 1, wherein the attaching means are selected from the group consisting of thread, cord, and wire.

24. The method according to claim 1, wherein the attaching means are constructed from material selected from the group consisting of (a) elastomeric materials and (b) shape-memory materials.

25. The method according to claim 1, wherein the attaching means comprise dual, substantially parallel elastic wires.

26. The method according to claim 25, wherein the dual, substantially parallel elastic wires are separated by separating means selected from the group consisting of pinch-point joints, joints, and flexible ties.

27. The method according to claim 1, wherein the attaching means comprise at least one bioerodable material.

28. The method according to claim 27, wherein the at least one bioerodible material is selected from the group consisting of polyesters, polyamides, polypeptides, polysaccharides, polylactides, polyglycolides, polyanhydrides, polyurethanes, polyesteramides, polyorthoesters, polydioxanones, polyacetyls, polyketals, polycarbonates, polyorthocarbonates, polyphosphazenes, polyhydroxybutyrates, polyhydroxyvalerates, polyalkylene oxalates, polyalkylene succinates, polymalic acid, poly(amino acids), polymethyl vinyl ether, polymaleic anhydride, chitin, chitosan, poly(1-lactic acid) (P1LA), poly (dl-lactic acid) (PLA), poly(glycolic acid) (PGA), polycaprolactones and their block and intimate copolymers, terpolymers and higher poly-monomer polymers thereof, polyvinylacetate and polyacrylic acid, methylcellulose, carboxymethylcellulose, hydroxypropylcellulose, and hydroxypropylmethylcellulose, polyvinyl acetyldiethylaminoacetate, cellulose acetatephthalate and ethyl cellulose, and copolymers of methacrylic acid and methyl methacrylate, hydroxypropylmethylcellulose (HPMC), hydroxypropylcellulose (HPC), carboxymethylcellulose, and sodium or calcium salts thereof, hydrogel, shape memory material, super elastic material, and nickel titanium (NiTi), combinations, and mixtures thereof; and wherein the at least one bioerodible material is integrated into a single combination or a mixture of several combinations thereof, and at least one layer is configured in the expandable envelope.

29. The method according to claim 1, further including layers configured in the expandable envelope to maintain expansion for the pre-selected period of time.

30. The method according to claim 1, wherein the gastric implant has an envelope including at least one bioerodable material.

31. The method according to claim 1, wherein the envelope is compacted by a method selected from the group consisting of rolling and folding.

32. The method according to claim 1, wherein a bioerodable capsule encloses the envelope and gas-producing composition.

33. The method according to claim 1, wherein the gastric implant includes a coating selected from the group consisting of a bioerodable coating for enclosing the envelope and gas-producing composition, an enteric coating enclosing the envelope and gas-producing composition, and combinations thereof.

34. The method according to claim 33, wherein the bioerodable coating comprises gelatin.

35. The method according to claim 1, wherein the gastric implant has a bioerodable shape stabilizer maintaining a compacted shape of the implant.

36. The method according to claim 1, wherein the inflating of step (b) further includes applying an external stimulus to initiate inflation of the gastric implant; the external stimulus selected from the group consisting of physical manipulation, an external magnetic field, digestive movements, application of radio-frequency energy, and combinations thereof.

37. The method according to claim 1, wherein the inflating of step (b) further includes externally manipulating the stomach of the patient in order to initiate inflation of the gastric implant.

38. The method according to claim 1, wherein the inflating of step (b) further includes bringing to a predetermined value a condition selected from the group consisting of temperature, pH, water activity ($a_w$), water availability in the stomach, and availability of digestive enzymes in order to initiate inflation of the gastric implant.

39. The method according to claim 1, further comprising a step (c) of disassembling the gastric implant after a predetermined period of time; wherein the disassembling includes a step selected from the group consisting of at least partially deflating the gastric implant; at least partially dissolving at least part of a material of the gastric implant; at least partially eroding at least a part of the material of the gastric implant; at least partially disintegrating at least part of the material of the gastric implant into smaller pieces; at least partially digesting the gastric implant, and combinations thereof.

40. The method according to claim 1, wherein the gastric implant is selected from the group consisting of an implant having grooves on an external surface, the grooves adapted to accelerate rate of disassembling the gastric implant; an implant having protrusions on an external surface, the protrusions adapted to accelerate rate of disassembling the gastric implant; and combinations thereof.

41. A method of treating obesity comprising steps of:
  a. curbing the appetite of an obese patient according to the method of claim 1; and,
  b. repeating step (a) at times determined by a predetermined protocol;
  wherein an amount of food ingested by the patient while the implant is within the stomach of the patient is less than that ingested prior to commencement of the method.

42. The method according to claim 41, further comprising leaving the gastric implant within the stomach of the patient for a predetermined period of time.

43. The method according to claim 1, wherein the gastric implant is adapted to provide a predetermined amount of pressure against a wall of the stomach upon inflation.

44. The method according to claim 43, wherein the predetermined amount of pressure is a maximum pressure obtainable for a given quantity of gas-producing composition.

45. The method according to claim 1, wherein the gastric implant includes at least one adjuvant composition selected from the group consisting of therapeutic compositions, slow-release therapeutic compositions, medications, pH buffers, anti-acid compositions, anti-inflammatory agents, antihistamines, additives, lubricants, ultraviolet contrasting agents, ultrasound contrasting agents, radio-opacifiers, diagnostic agents, digestive-related therapeutic agents, probiotic bacteria cultures, and combinations thereof.

46. The method according to claim 45, wherein the adjuvant composition is selected from the group consisting of an adjuvant composition at least partially infused into the implant, an adjuvant composition mixed with the implant, an adjuvant composition coated onto the implant, and combinations thereof.

47. The method according to claim 1, wherein creating a feeling of fullness and curbing the appetite of the patient is obtained after inflating the gastric implant and after the patient introduced food into the stomach.

\* \* \* \* \*